US011268949B2

(12) United States Patent
Suzuki et al.

(10) Patent No.: US 11,268,949 B2
(45) Date of Patent: Mar. 8, 2022

(54) BLOOD ANALYSIS METHOD, BLOOD ANALYZER, AND NON-TRANSITORY COMPUTER READABLE MEDIUM

(71) Applicants: SYSMEX CORPORATION, Kobe (JP); University of Yamanashi, Kofu (JP)

(72) Inventors: Takeshi Suzuki, Kobe (JP); Yutaka Komiyama, Kobe (JP); Hiroshi Kurono, Kobe (JP); Sho Shinohara, Kobe (JP); Kaneo Satoh, Kofu (JP); Fuminori Kazama, Kofu (JP); Yugo Shimada, Kofu (JP)

(73) Assignees: SYSMEX CORPORATION, Kobe (JP); UNIVERSITY OF YAMANASHI, Kofu (JP)

( * ) Notice: Subject to any disclaimer, the term of this patent is extended or adjusted under 35 U.S.C. 154(b) by 337 days.

(21) Appl. No.: 16/385,295

(22) Filed: Apr. 16, 2019

(65) Prior Publication Data

US 2019/0331659 A1 Oct. 31, 2019

(30) Foreign Application Priority Data

Apr. 26, 2018 (JP) .............................. JP2018-085132

(51) Int. Cl.
*G01N 33/86* (2006.01)
*G01N 33/49* (2006.01)
*G01N 21/75* (2006.01)
*G01N 21/31* (2006.01)
*G01N 21/17* (2006.01)

(52) U.S. Cl.
CPC ......... *G01N 33/4905* (2013.01); *G01N 21/75* (2013.01); *G01N 33/86* (2013.01); *G01N 21/3151* (2013.01); *G01N 2021/1736* (2013.01); *G01N 2021/755* (2013.01)

(58) Field of Classification Search
CPC ..... G01N 2021/1736; G01N 2021/755; G01N 2021/7783; G01N 2035/00356; G01N 2035/0097; G01N 2035/0443; G01N 2035/0444; G01N 21/3151; G01N 21/75; G01N 21/82; G01N 33/4905; G01N 33/86
USPC ........... 436/63, 69, 164, 177; 422/73, 82.05, 422/82.09; 435/13; 73/64.41, 64.43; 600/369

See application file for complete search history.

(56) References Cited

U.S. PATENT DOCUMENTS

| | | | |
|---|---|---|---|
| 6,027,904 A | 2/2000 | Devine et al. | |
| 7,962,292 B2* | 6/2011 | Matsuo | G01N 15/1459 702/22 |
| 8,445,287 B2* | 5/2013 | Carroll | G01N 21/272 436/69 |
| 8,936,753 B2* | 1/2015 | Yamamoto | G01N 35/00603 422/73 |
| 9,213,037 B2* | 12/2015 | Kurono | G01N 33/86 |
| 9,933,443 B2* | 4/2018 | Kumano | G01N 33/4905 |
| 10,215,766 B2* | 2/2019 | Shima | G01N 33/4905 |
| 10,739,360 B2* | 8/2020 | Suzuki | G01N 33/86 |
| 2011/0002526 A1 | 1/2011 | Fairvre et al. | |
| 2014/0255254 A1 | 9/2014 | Yamaguchi et al. | |
| 2017/0030891 A1 | 2/2017 | Brun et al. | |

FOREIGN PATENT DOCUMENTS

| | | |
|---|---|---|
| EP | 2 246 691 A1 | 11/2010 |
| FR | 2 945 350 A1 | 11/2010 |
| JP | 2014173904 A | 9/2014 |
| WO | 2010/128221 A1 | 11/2010 |
| WO | 2015/159623 A1 | 10/2015 |

OTHER PUBLICATIONS

Extended European Search Report dated Aug. 16, 2019, by the European Patent Office in corresponding European Patent Application No. 19170878.3. (7 pages).
Machine English translation of FR2945350, previously cited on Aug. 29, 2019. (18 pages).
Ieko et al., "Expert consensus on standardization of sample preparation for clotting time assays," Journal of The Japanese Society for Laboratory Hematology, (2016), vol. 17, No. 2, pp. 149-157, and an English translation thereof (16 pages).
Communication pursuant to Article 94(3) EPC dated Oct. 26, 2020, by the European Patent Office in corresponding European Patent Application No. 19 170 878.3. (4 pages).
Notice of Reasons for Refusal dated Jan. 25, 2022, by the Japanese Patent Office in corresponding Japanese Patent Application No. 2018-085132 and an English translation of the Notice. (8 pages).

\* cited by examiner

*Primary Examiner* — Maureen Wallenhorst
(74) *Attorney, Agent, or Firm* — Buchanan, Ingersoll & Rooney PC

(57) ABSTRACT

A blood analysis method includes: acquiring optical information which changes over time from a mixed liquid of a blood sample and a reagent for coagulation time measurement after mixing the blood sample and the reagent, and acquiring information related to a coagulation time and information related to a number of platelets in the blood sample based on the acquired optical information.

19 Claims, 20 Drawing Sheets

Modification

Modification

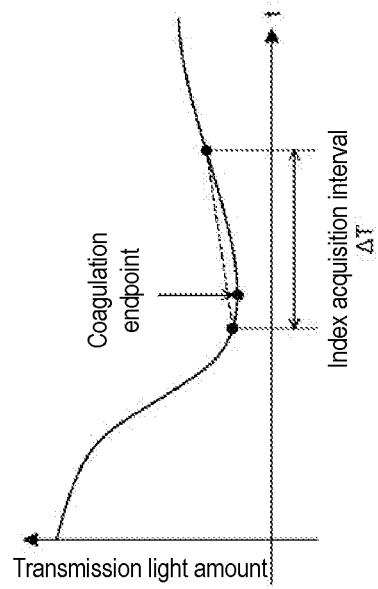
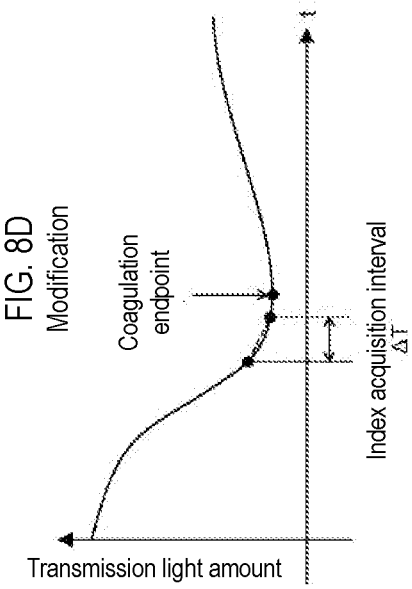
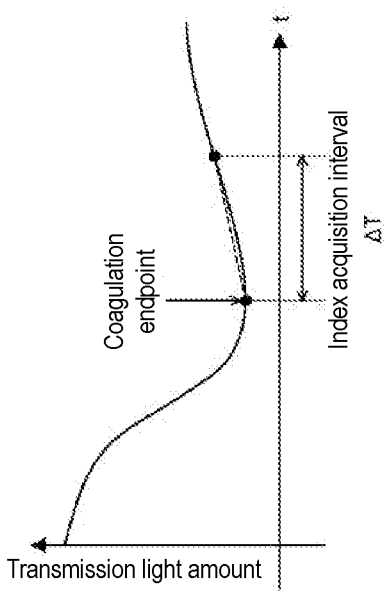
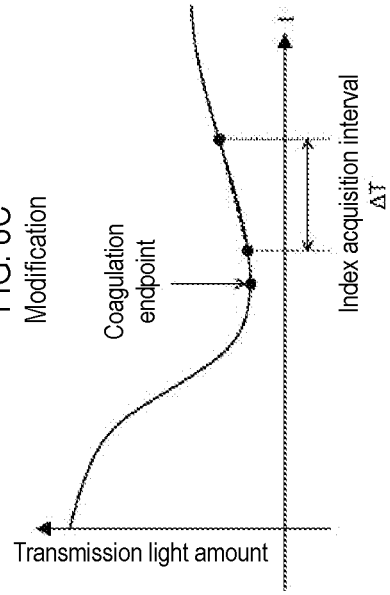

| State | Sample No. | End time | Start time | Date | PT | Fib | LA |
|---|---|---|---|---|---|---|---|
| | 0001 | 11:18 | 11:10 | 2018/03/30 | ..... | ..... | ..... |
| Review | 0002 | 11:19 | 11:11 | 2018/03/30 | ..... | ..... | — |
| Review | 0003 | 11:20 | 11:12 | 2018/03/30 | ..... | ..... | — |
| | 0004 | 11:21 | 11:13 | 2018/03/30 | ..... | ..... | ..... |
| | 0005 | 11:22 | 11:14 | 2018/03/30 | ..... | ..... | ..... |
| | 0006 | 11:23 | 11:15 | 2018/03/30 | ..... | ..... | ..... |
| | 0007 | 11:24 | 11:16 | 2018/03/30 | ..... | ..... | ..... |

Display detail

FIG. 10

BLOOD ANALYSIS METHOD, BLOOD ANALYZER, AND NON-TRANSITORY COMPUTER READABLE MEDIUM

CROSS REFERENCE TO RELATED APPLICATIONS

This application claims priority from prior Japanese Patent Application No. 2018-085132, filed on Apr. 26, 2018, entitled "BLOOD ANALYSIS METHOD, BLOOD ANALYZER, AND PROGRAM", the entire contents of which are incorporated herein by reference.

FIELD OF THE INVENTION

The present invention relates to a blood analysis method, blood analyzer, and non-transitory computer readable medium.

BACKGROUND

Japanese Patent Application Publication No. 2014-173904 discloses a blood coagulation analyzer that analyzes a coagulability of blood by irradiating light on a measurement sample prepared by adding a reagent to a plasma sample and analyzing a light transmitted through the measurement sample.

A plasma sample to be supplied to the blood coagulation analyzer as described above is obtained by subjecting a whole blood sample to centrifugal separation treatment. Here, according to the Journal of the Japan Society for Laboratory Hematology, vol. 17, No. 2, "Consensus on Coagulation Test Sample Handling", a number of remaining platelets of the plasma sample is preferably less than 10,000 cells/µL, and centrifugal separation is preferably performed at 1500 g or more for 15 minutes or longer in order to avoid influencing a measurement result.

However, the centrifugation performed by the user is not necessarily performed properly under the above-mentioned conditions, and depending on a pathological condition of the subject, there are cases where the number of platelets in the plasma sample is great. Therefore, the number of remaining platelets in the plasma sample provided to the apparatus is not necessarily below the number mentioned above. For these reasons, it is desirable for the blood coagulation analyzer to be able to ascertain the influence of the number of platelets on the measurement result.

SUMMARY OF THE INVENTION

A first aspect of the present invention relates to a blood analysis method. In the blood analysis method according to this aspect, after mixing a blood sample and a reagent for coagulation time measurement, optical information that changes over time is acquired from the mixed liquid of the blood sample and the reagent, and information related to the coagulation time and information related to a number of platelets in the blood sample are acquired based on the acquired optical information.

The inventors found that a state of change in optical information varies depending on the number of platelets in a blood sample. Based on this finding, the inventors also found that the state of the number of platelets in the blood sample can be estimated based on the optical information. Therefore, according to the blood analysis method of this aspect, information based on the number of platelets in the blood sample can be acquired by the above method. By referring to this information, the operator can grasp the influence of the number of platelets on the measurement result. The information related to the coagulation time is information obtained in routinely performed coagulation tests, and is, for example, a coagulation time and a concentration obtained based on the coagulation time. According to the blood analysis method of this aspect, it is also possible to acquire information based on the number of platelets while acquiring information related to the coagulation time.

In the blood analysis method according to this aspect, the information related to the number of platelets in the blood sample is acquired based on the optical information at an end stage of a coagulation reaction of the blood sample among the acquired optical information. The inventors found that the state of change in optical information at the end of the coagulation reaction varies depending on the number of platelets in the blood sample. Therefore, according to the optical information at the end stage of the coagulation reaction, the information related to the number of platelets in the blood sample can be acquired more accurately.

In the blood analysis method according to this aspect, a coagulation end point is detected from the acquired optical information, and the information related to the number of platelets in the blood sample is acquired based on the optical information in a predetermined time range including a timing after the coagulation ending point. The inventors found that the state of change of optical information within a predetermined time range including the timing after the coagulation end point reflects the number of platelets in the blood sample. Hence, the information related to the number of platelets in the blood sample can be acquired more accurately according to the optical information in the predetermined time range.

In the blood analysis method according to this aspect, the information related to the number of platelets in the blood sample includes information on the number of platelets or the necessity of additional treatment on the blood sample. When the number of platelets is acquired as the information related to the number of platelets, the operator can grasp the degree to which platelets are contained in the blood sample. Additional treatment includes, for example, reacquisition of the blood sample and re-centrifugation of blood sample. When information on the necessity of additional treatment is acquired as the information related to the number of platelets, the operator can determine whether it is necessary to reacquire the blood sample in a proper state.

In the blood analysis method according to this aspect, optical information is acquired based on a first measurement related to the measurement of the coagulation time, and the information related to the number of the platelets in the blood sample includes information related to the influenced on a second measurement that is different from the first measurement. If there is a large number of platelets in the blood sample, the result of the second measurement may be inappropriate in some cases even if the result of the first measurement is appropriate. In this case, when information concerning the influence on the second measurement is acquired as information based on the number of platelets, the operator can determine whether the result of the second measurement is appropriate.

In the blood analysis method according to this aspect, an index value indicating a change of state of the optical information is acquired based on the optical information in a predetermined time range, and the information related to the number of platelets in the blood sample is acquired based on the index value.

In this case, the index value is a change rate or a change amount of the optical information within a predetermined time range. In this way it is possible to easily grasp the change of state of the optical information within the predetermined time range.

In this case, the change rate or the change amount is acquired based on the optical information at a start point and an end point of the predetermined time range.

In the blood analysis method according to this aspect, the information related to a level of the platelet count in the blood sample is acquired based on the number of platelets in the blood sample by comparing the index value with one or more first reference values set in advance. The acquired value reflects the optical information in the predetermined time range and varies according to the number of platelets in the blood sample. Therefore, by referring to the information related to the level of the platelet count in the blood sample, the operator can determine whether the number of platelets in the blood sample exceeds a reference value.

In the blood analysis method according to this aspect, a platelet count in the blood sample is acquired as the information related to the number of platelets in the blood sample based on the index value. In this way, the operator can directly determine the influence of the number of platelets on the measurement result since the number of platelets in the blood sample can be obtained.

In this case, the number of platelets in the blood sample is acquired from the index value using information indicating a correlation between the index value and the platelet count.

In the blood analysis method according to this aspect, information related to a level of the platelet count in the blood sample is acquired as the information related to the number of platelets by comparing the platelet count in the blood sample with one or more second reference values set in advance. When one second reference value is used, the second reference value is, for example, 10,000 platelets/µL. When three second reference values are used, the three second reference values are, for example, 10,000 platelets/µL, 30,000 platelets/µL, 50,000 platelets/µL. Therefore, by referring to the information related to the level of the platelet count in the blood sample, the operator can determine whether the platelet count in the blood sample exceeds the reference value.

In the blood analysis method according to this aspect, information that suggesting a presence of measurement items affected by platelets in the blood sample or information related to a necessity of additional treatment of the blood sample is acquired based on the number of platelets in the blood sample or on information based on the number of platelets in the blood sample. By using the number of platelets in the blood sample, it is possible to smoothly obtain information indicating the presence of measurement items affected by platelets or the information on the necessity of additional treatment.

In the blood analysis method according to this aspect, the information related to the number of platelets in the blood sample is displayed on a display means. In this way the operator can visually grasp the information related to the number of platelets in the blood ample.

In the blood analysis method according to this aspect, the optical information is acquired in a step of measuring the coagulation time of the blood sample. In this way, the information related to the number of platelets in the blood sample can be acquired based on the step of measuring the coagulation time of the blood sample, and the coagulation time can also be calculated in this step.

In this case, the coagulation end point is an end point of a time range used for calculating the coagulation time of the blood sample.

In the blood analysis method according to this aspect, a start point of the predetermined time range is set after the coagulation ending point.

In the blood analysis method according to this aspect, a length of the predetermined time range is 5 seconds or more and 10 seconds or less.

A second aspect of the present invention relates to a blood analyzer. A blood analyzer according to this aspect includes a measuring unit for irradiating light to a mixed liquid in which a blood sample and a reagent for coagulation time measurement are mixed and for detecting light generated from the mixed liquid, and a processing unit for processing a result detected by the measuring unit. After mixing the blood sample and the reagent, the processing unit acquires optical information that changes over time from the mixed liquid, and acquires information related to a coagulation time and information related to a number of platelets in the blood sample based on the acquired optical information.

According to the blood analyzer of this aspect, the same effect as that of the first aspect is obtained.

A third aspect of the present invention relates to a non-transitory computer readable medium storing programs executable by a processor. The non-transitory computer readable medium according to this aspect includes receiving optical information that changes over time from a mixed liquid of a blood and a reagent for coagulation time measurement after mixing the blood sample and the reagent, and acquiring information related to a coagulation time and information relating to a number of a platelets in the blood sample based on the acquired optical information.

According to the program of this aspect, the same effects as those of the first aspect are obtained.

BRIEF DESCRIPTION OF THE DRAWINGS

FIG. 8A is a diagram showing an index value acquisition section according to the first embodiment; FIGS. 8B to 8D are diagrams showing the index value acquisition intervals according to the modification;

FIG. 10 is a diagram schematically showing a configuration of a screen displayed on a display unit according to the first embodiment;

DESCRIPTION OF THE EMBODIMENTS OF THE INVENTION

First Embodiment

The outline of the first embodiment will be described referring to FIG. 1 and FIG. 2.

Figure 1:
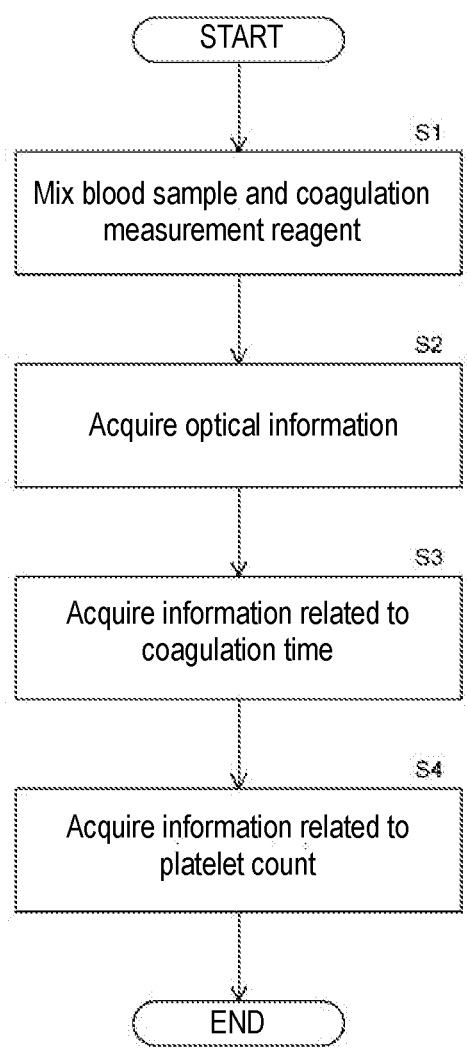
FIG. 1 is a flowchart showing a blood analysis method according to an outline of a first embodiment.

The flowchart shown in FIG. 1 shows a process of measuring in a blood coagulation analysis process, and acquiring information based on the number of platelets by using the optical information obtained in this measurement. The process of FIG. 1 is executed by the blood analyzer 10 shown in FIG. 2.

Figure 2:
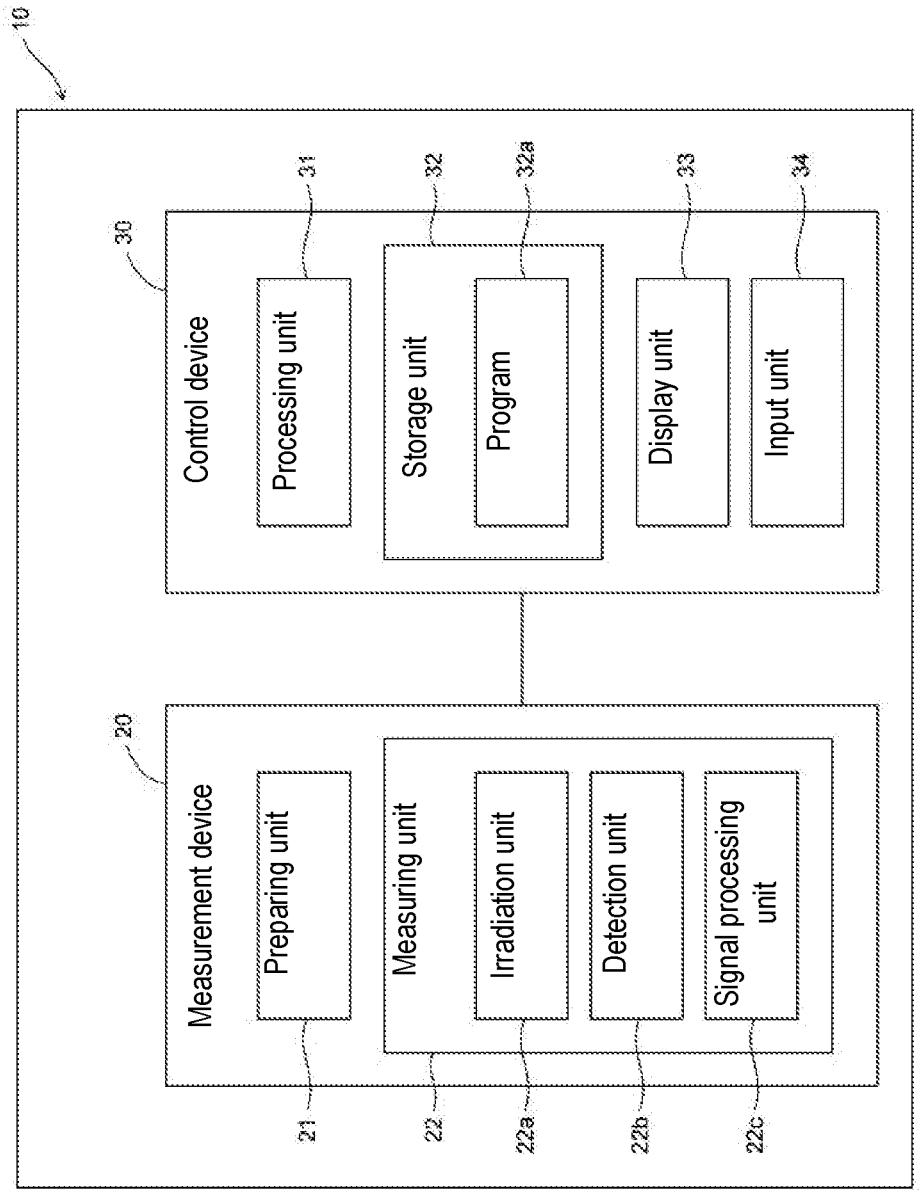
FIG. 2 is a block diagram showing a configuration of a blood analyzer according to the outline of the first embodiment.

As shown in FIG. 2, the blood analyzer 10 includes a measurement device 20 and a control device 30. The blood analyzer 10 irradiates light on a blood sample prepared by adding a reagent to a blood specimen and acquires measurement results of a plurality of measurement items by analyses related to coagulability of the blood sample by analyzing the acquired transmission light by a coagulation method, a synthetic substrate method, an immunoturbidimetric method, and an agglutination method.

The measuring device 20 includes a preparation unit 21 and a measuring unit 22. The preparation unit 21 dispenses a blood specimen from a specimen container, warms the dispensed blood specimen, adds a reagent to the warmed blood specimen to prepare a blood sample. The measuring unit 22 includes an irradiation unit 22a, a detection unit 22b, and a signal processing unit 22c. The irradiation unit 22a irradiates light on the blood sample prepared by the preparation unit 21. The irradiation unit 22a is, for example, a halogen lamp or an LED. The detection unit 22b receives the transmission light transmitted through the blood sample, among the light irradiated on the blood sample by the irradiation unit 22a. The detection unit 22b is, for example, a photodiode or an avalanche photodiode. Note that the detection unit 22b is not limited to receiving the transmission light from the blood sample, and also may receive the scattered light that is scattered by the blood sample.

As the coagulation reaction of the blood sample progresses, the turbidity of the blood sample increases, and the amount of transmitted light from the blood sample decreases as the turbidity increases. The detection unit 22b detects the process of coagulation of blood as a change in transmission light. In this case, when the coagulation reaction of the blood sample progresses, the amount of light received by the detection unit 22b generally decreases. Note that when the detection unit 22b receives the scattered light, the amount of light received by the detection unit 22b generally increases as the coagulation reaction of the blood sample progresses.

The signal processing unit 22c converts the detection signal output from the detection unit 22b to digital data by an AD converter, and transmits the digital data to the control device 30 as measurement data. The measurement data transmitted to the control device 30 are data that change over time in the detection period from the start to the end of the detection by the detection portion 22b. The measurement data are obtained by detecting the coagulation process of the blood sample as a change over time in the intensity of the transmission light and are the coagulation curve data. For example, the coagulation curve data have a sampling time interval of 0.1 seconds. The time from detection start to detection end is, for example, a maximum of 1 hour.

The control device 30 includes a processing unit 31, a storage unit 32, a display unit 33, and an input unit 34. The processing unit 31 is, for example, a CPU. The storage unit 32 is, for example, a RAM, a ROM, a hard disk, or the like. The storage unit 32 stores a computer program 32a to be executed by the processing unit 31.

The processing unit 31 processes the detection result of the measuring unit 22. Specifically, the processing unit 31 acquires the measurement data transmitted from the measurement device 20 as optical information, and stores the acquired optical information in a storage unit 32. As described above, the optical information are data indicating a change over time in the intensity of transmission light. Note that when the measurement data are obtained by detecting the coagulation process of the blood sample as a change over time in the intensity of the scattered light, the optical information are data indicating the change over time of the intensity of the scattered light. The processing unit 31 also may calculate the light absorbance based on the measurement data transmitted from the measurement device 20, and may acquire the calculated absorbance as optical information.

The display unit 33 is, for example, a liquid crystal display. The input unit 34 is a mouse and a keyboard. Note that the display unit 33 and the input unit 34 also may be integrated in the manner of a touch panel type display.

Returning to FIG. 1, in Step S1, the measurement device 20 mixes the blood specimen and the reagent for measuring the coagulation time and performs a measurement. The measurement data obtained by the measurement is transmitted to the control device 30. In step S2, the processing unit 31 of the control device 30 acquires the optical information. In step S3, the processing unit 31 acquires information on the coagulation time based on the optical information acquired in step S2. The information relating to the coagulation time is information obtained in a routinely performed coagulation test, and is, for example, the coagulation time and the concentration obtained on the basis of the coagulation time. In step S4, the processing unit 31 acquires information based on the number of platelets in the blood sample based on the optical information acquired in step S2.

As a result of various verifications, the inventors found that the state of change in optical information varies depending on the number of platelets in a blood sample. Based on this finding, the inventors also found that the state of the number of platelets in the blood sample can be estimated based on the optical information. Therefore, by performing the process shown in FIG. 1, information based on the number of platelets in the blood sample can be acquired. By referring to this information, the operator can grasp the influence of the number of platelets on the measurement result.

When the processes in steps S1 to S4 are performed, information based on the number of platelets also can be acquired while acquiring information on the coagulation time. That is, it is possible to acquire information based on the number of platelets at the same time simultaneously with a routinely performed coagulation test. Since it is unnecessary to perform a measurement different from the routinely performed measurement in order to acquire information based on the platelet count, a series of coagulation tests can be performed quickly, and it is possible to avoid situations such as requiring separate reagents and the like in order to acquire information based on the number of platelets.

Next, the blood analysis method of the first embodiment will be described in detail.

Figure 3:
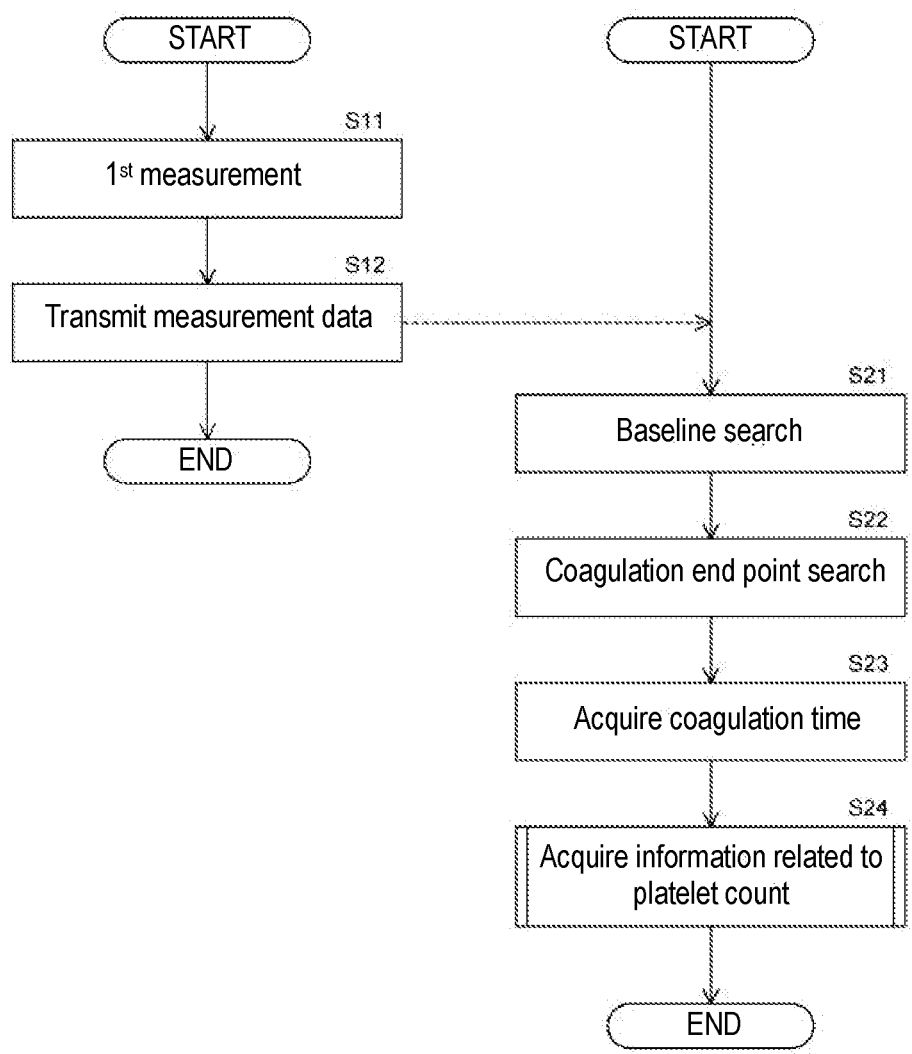
FIG. 3 is a flowchart showing a blood analysis method according to the first embodiment.

In the flowchart shown in FIG. 3, a measurement for calculating the prothrombin time (PT) is performed using the coagulation method in the blood coagulation analysis processing, and information based on the number of platelets is acquired using the optical information obtained in this measurement. The process of FIG. 3 indicates the process shown in FIG. 1 in detail, and is executed by the blood analyzer 10 shown in FIGS. 2 and 4.

In the first embodiment, information based on the number of platelets is acquired using the optical information obtained by the measurement for calculating the prothrombin time. The optical information used for acquiring information based on the number of platelets is not necessarily limited to the optical information acquired by the measurement for calculating the prothrombin time. For example, measurement for calculating fibrinogen activity also may be performed, and information based on the number of platelets may be obtained using the optical information acquired in this measurement.

Figure 4:
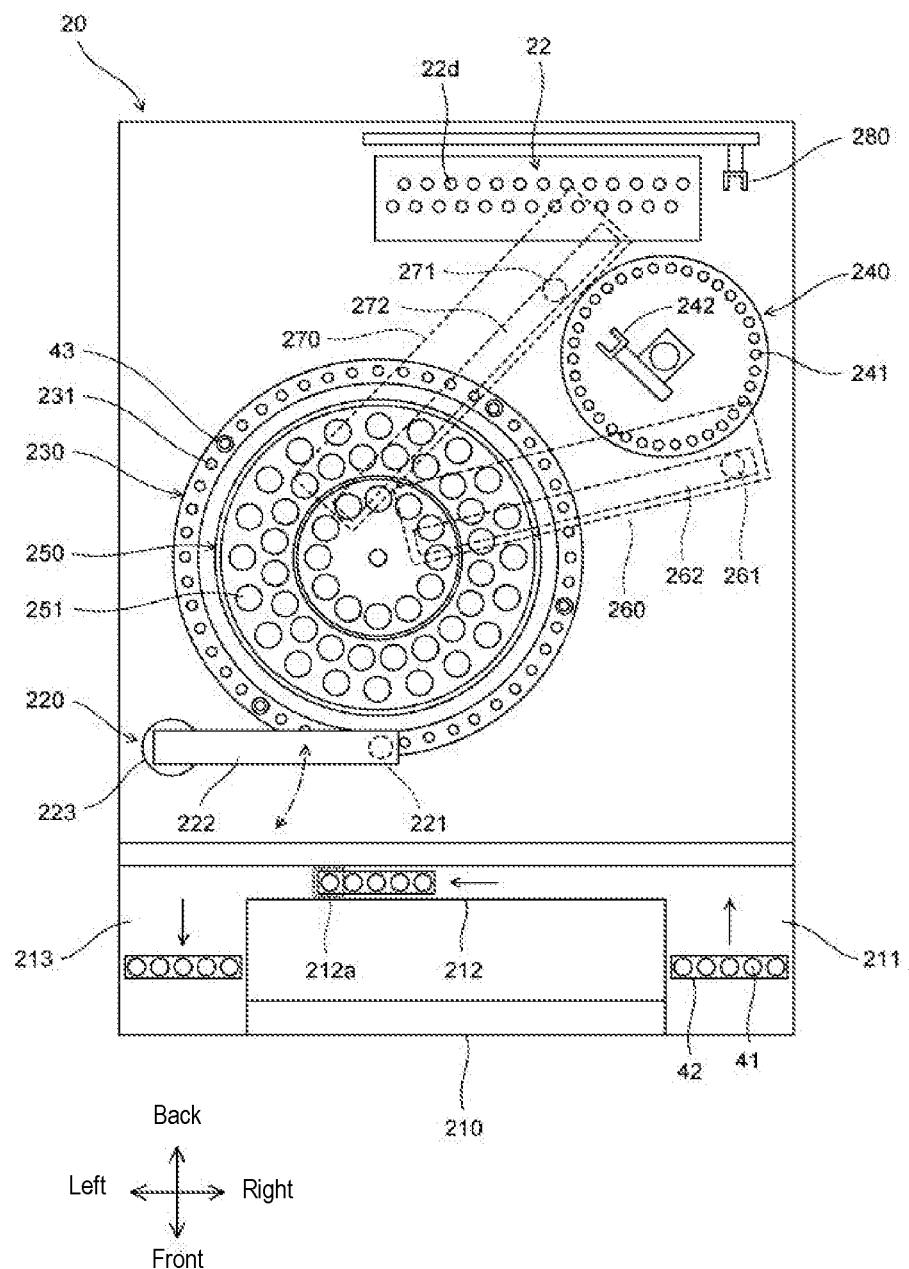
FIG. 4 is a plan view schematically showing a configuration of a measuring apparatus according to the first embodiment.

FIG. 4 is a diagram showing a configuration when the measurement device 20 shown in FIG. 2 is viewed from above. The measurement device 20 includes the configuration shown in FIG. 4 in addition to the configuration shown in FIG. 2.

As shown in FIG. 4, the measurement device 20 includes a transport unit 210, a sample dispensing unit 220, a reaction container table 230, a heating table 240, a reagent table 250, reagent dispensing units 260 and 270, a transport unit 280, and a measuring unit 22.

The transport unit 210 includes a rack setting unit 211, a rack transport unit 212, and a rack collection unit 213. The operator sets a sample container 41 containing the blood sample in the sample rack 42, and sets the sample rack 42 in the rack setting unit 211. The transport unit 210 transports the sample rack 42 installed in the rack setting unit 211 to the rack transport unit 212, and sequentially positions the sample containers 41 at the sample suction position 212a. When the suction is completed for the samples of all the sample containers 41 held by the sample rack 42, the transport unit 210 transports the sample rack 42 to the rack collection unit 213.

The sample dispensing unit 220 includes a nozzle 221, an arm 222, and a mechanical unit 223. The nozzle 221 is installed at the tip of the arm 222. The mechanical unit 223 is configured to rotate the arm in the circumferential direction and to move it in the vertical direction. In this way the nozzle 221 can move in the circumferential direction and the vertical direction. The sample dispensing section 220 suctions the blood sample from the sample container 41 positioned at the sample suction position 212a, and discharges the suctioned sample to the reaction vessel 43 held in a holding hole 231 of the reaction container table 230.

The reaction container table 230 has an annular shape in plan view and is disposed on the outer side of the reagent table 250. The reaction container table 230 is configured to be rotatable in the circumferential direction. The reaction container table 230 has a plurality of holding holes 231 for holding the reaction container 43.

The heating table 240 includes a plurality of holding holes 141 for holding the reaction containers 43, and a transfer unit 242 for transferring the reaction containers 43. The heating table 240 has a circular contour in plan view and is configured to be rotatable in the circumferential direction. The heating table 240 heats the reaction vessel 43 set in the holding hole 241 to 37° C.

When the blood sample is discharged to the reaction container 43 held in the reaction container table 230, the reaction container table 230 is rotated, and the reaction container 43 containing the blood sample is transferred to the vicinity of the heating table 240. Then, the transfer unit 242 of the heating table 240 grips the reaction container 43 and sets the container 43 in the holding hole 241 of the heating table 240.

The reagent table 250 is configured to be able to install a plurality of reagent containers 251 containing reagents used for measurement relating to the blood coagulation test. The reagent table 250 is configured to be rotatable in the circumferential direction. A plurality of reagent containers 251 containing reagents used in the measurement of the measurement items are installed in the reagent table 250, and for example, a reagent container 251 containing a reagent for measuring prothrombin time and a reagent container 251 containing reagents for fibrinogen measurement 251 and the like are installed therein.

The reagent dispensing unit 260 includes a nozzle 261 and a mechanical unit 262. The mechanical unit 262 is configured to move the nozzle 261 horizontally so as to traverse the reagent table 250 and to move the nozzle 261 in the vertical direction. Similarly, the reagent dispensing unit 270 includes a nozzle 271 and a mechanical unit 272. The mechanical unit 272 moves the nozzle 271 in the horizontal direction so as to traverse the reagent table 250 and also moves the nozzle 271 in the vertical direction. The reagent dispensing units 260 and 270 are installed on the lower side of the upper surface of the housing of the measurement device 20.

The reagent dispensing units 260 and 270 dispense the reagent to the reaction vessel 43 heated by the heating table 240. Upon dispensing the reagent, the transfer unit 242 or the transport unit 280 removes the reaction container 43 from the holding hole 241 of the heating table 240, and positions the container 43 at a predetermined position in the vicinity of the heating table 240. Then, the reagent dispensing units 260 and 270 draw the reagent from the reagent container 251 via the nozzles 261 and 271, and discharge the suctioned reagent to the reaction container 43. In this way the reagent is mixed with the blood sample to prepare a blood sample. The preparation unit 21 in FIG. 2 corresponds to the heating table 240, the reagent table 250, the reagent dispensing units 260 and 270, and the transport unit 280. Thereafter, the transport unit 280 sets the reaction container 43 in the holding hole 22d of the measuring unit 22.

The measuring unit 22 includes a plurality of holding holes 22d. The measuring unit 22 irradiates light on the reaction container 43 set in the holding hole 22d by the irradiation unit 22a, and receives the light transmitted through the blood sample by the detection unit 22b.

Returning to FIG. 3, in step S11, the measurement device 20 performs the first measurement based on the blood sample. In the first embodiment, the first measurement is a measurement relating to the measurement item "PT" and is a measurement for calculating the prothrombin time. Note that the first measurement also may be a measurement relating to the measurement item "Fbg" and may be a measurement for calculating the fibrinogen activity. The blood sample to be used for the first measurement is plasma obtained by centrifuging a whole blood specimen collected from a subject. Whole blood specimen collected from the subject is contained in a sample container 41 containing sodium citrate. By centrifuging this sample container 41, plasma from which blood cell components have been removed from citrated plasma is obtained.

Note that the blood sample to be subjected to the first measurement is not limited to blood plasma, and also may be whole blood, for example. Also in this case, the first measurement may be a measurement for measuring the coagulation time.

Specifically, in step S11, the process is performed as follows. The sample dispensing unit 220 suctions the blood sample from the sample container 41 transported by the transport unit 210, and discharges the suctioned sample to the reaction container 43 of the reaction container table 230. The reaction container 43 is transferred by the reaction container table 230 and the transfer unit 242 and set in the holding hole 241 of the heating table 240. The heating table 240 heats the blood sample in the reaction container 43. The transfer unit 280 removes the reaction container 43 from the holding hole 241 and positions the container 43 at a position for dispensing the reagent. The reagent dispensing unit 270 dispenses a reagent for measuring the prothrombin time into the reaction container 43 held by the transfer unit 280. In this way a mixed solution of the blood sample and the reagent for measuring the prothrombin time, that is, a blood sample for the first measurement is prepared.

The reagent for measuring the prothrombin time is, for example, a thromboplastin-containing reagent, specifically, Tromborel S and Thrombocheck PT manufactured by Sysmex Corporation. Note that when the first measurement is a measurement relating to the measurement item "Fbg", the preparation unit 21 mixes the blood sample and the reagent for measuring fibrinogen to prepare a blood sample for the first measurement. The reagent for measuring fibrinogen is, for example, a thrombin-containing reagent, specifically, thrombocheck Fib (L) manufactured by Sysmex Corporation or the like. The reagent dispensing unit 270 suctions the reagent used in the first measurement from the reagent container 251, and discharges the suctioned reagent into the reaction container 43 containing the blood sample to prepare a blood sample.

When the reagent dispensing unit 270 dispenses the reagent, the transfer unit 280 sets the reaction container 43 in the holding hole 22d. The measuring unit 22 irradiates light of 660 nm on the blood sample for the first measurement by the irradiation unit 22a, and receives the transmission light transmitted through the blood sample by the detection unit 22b. The measuring unit 22 processes the detection signal output from the detection unit 22b by the signal processing unit 22c to acquire measurement data. Note that when the first measurement is measurement related to the measurement item "Fbg", the measuring unit 22 irradiates light of 405 nm on the blood sample by the irradiation unit 22a. In step S12, the measurement device 20 transmits the measurement data acquired in step S11 to the control device 30.

When the first measurement is performed using the reagent for measuring the prothrombin time and the reagent for measuring the fibrinogen, information based on the number of the platelets in the blood sample can be acquired based on the optical information in the predetermined time range as shall be described later. Since the optical information is acquired in the first measurement such as the measurement item "Fbg" or "Fib", that is, in the measurement step for measuring the coagulation time of the blood sample, information based on the number of platelets can be acquired based on this step, and the coagulation time also can be calculated in this step.

In steps S21 to S23, the processing unit 31 of the control device 30 executes a process of calculating the time until the coagulation reaction ends, that is, the prothrombin time based on the first measurement, on the basis of the measurement data received from the measurement device 20.

Here, the procedure of steps S21 to S23 will be described with reference to FIG. 5 and FIG. 6A.

Figure 5:
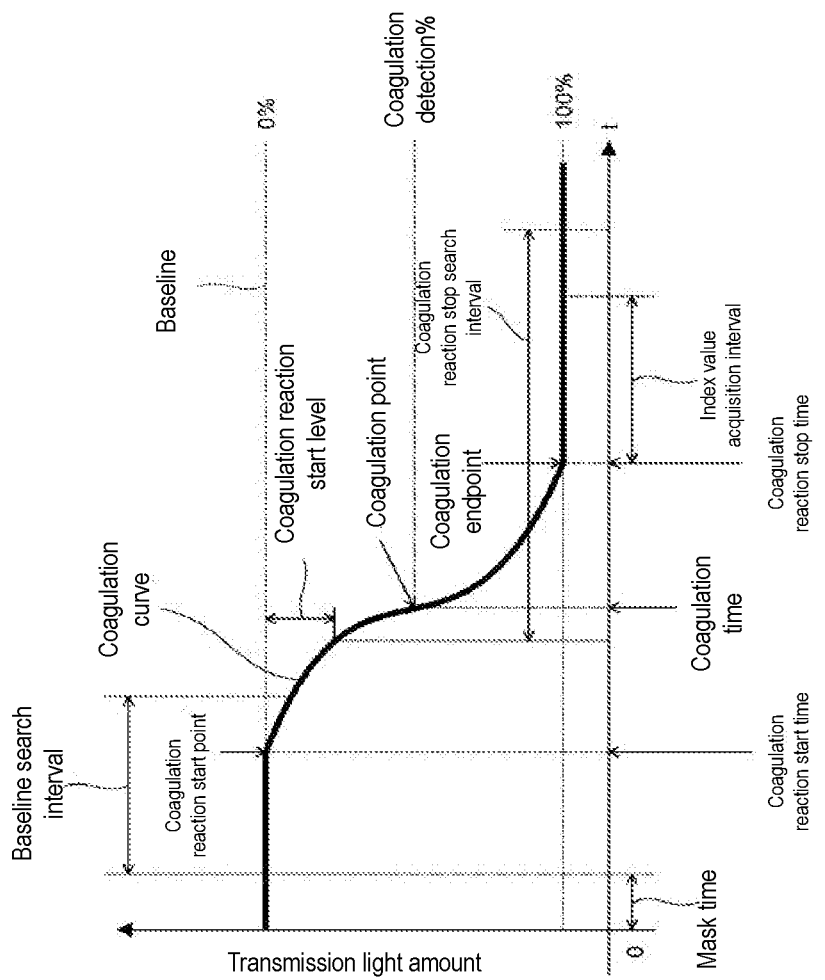
FIG. 5 is a diagram describing the acquisition of coagulation time performed by a processing unit of a control device according to the first embodiment.

FIG. 5 shows the basic shape of the coagulation curve used for calculating the time until the coagulation reaction is completed. As shown in FIG. 5, the shape of a general coagulation curve is, for example, a shape along a sigmoid curve. The coagulation curve is a curve having a first shape in which the value of the ordinate decreases as the value of the abscissa increases, and a curve having a second shape in which the value of the ordinate increases as the value of the abscissa increases Including. The shape shown in FIG. 5 is the first shape.

Note that when the measurement data are based on the transmission light amount, the general coagulation curve is the first shape shown in FIG. 5, and when the measurement data are based on the scattered light amount, the general coagulation curve becomes the second shape. Also, when absorbance is calculated from measurement data based on the amount of transmitted light, the general curve of absorbance becomes the second shape, and when absorbance is calculated from measured data based on the scattered light amount, the general absorbance curve is the first shape.

As shown in FIG. 5, in the case of a general coagulation curve with no abnormality, the amount of transmission light before starting the coagulation reaction is substantially constant. As the coagulation reaction starts, the amount of transmitted light decreases. Also, in the case of a general coagulation curve without abnormality, the amount of transmitted light after stopping the coagulation reaction is substantially constant.

The coagulation time is calculated on the premise that the coagulation curve assumes a shape as shown in FIG. 5. FIG. 5 shows a percentage detection method as an example of calculating the coagulation time. In the percentage detection method, the amount of transmitted light that is the baseline of the coagulation reaction starting point is 0%, the amount of transmitted light at the coagulation reaction end point, that is, the coagulation endpoint is 100%, and the time when the transmitted light amount reaches the coagulation detection % is defined as the coagulation time. The coagulation detection % is set as a predetermined ratio value relative to the interval between the transmission light amount at the baseline and the transmission light amount at the coagulation reaction end point. The coagulation detection % is used to search for a coagulation point where the amount of transmitted light has changed from the baseline by the coagulation detection %. The coagulation detection % is set to a value larger than 0% and smaller than 100%. The coagulation detection % is set to, for example, 50%.

The processes of steps S21 to S24 shown in FIG. 3 are performed by the processing unit 31 executing the program 32a.

In step S21 of FIG. 3, the processing unit 31 searches for a point at which the amount of transmission light becomes maximum, that is, a coagulation reaction starting point in the baseline search interval of FIG. 5 in the coagulation curve data based on the received measurement data. The baseline search interval is set to a predetermined period from the start of detection. The baseline search interval is, for example, a period from detection start to 60 seconds and is a period excluding a predetermined mask time set immediately after detection start. Of the coagulation curve data, data corresponding to the baseline search interval are used for baseline search. Note that the mask time is, for example, approximately several seconds. The processing unit 31 determines the amount of transmission light at the searched coagulation reaction starting point as a baseline.

In step S22 of FIG. 3, the processing unit 31 searches for the coagulation endpoint in the coagulation curve data as a point at which the coagulation reaction stops. The coagulation endpoint is the end point of the time range used for calculating the coagulation time of the blood sample based on the first measurement. The coagulation endpoint is searched for in the coagulation reaction stop search interval which is the period after the timing at which the difference between the baseline and the transmission light amount exceeds the predetermined coagulation reaction start level. Among the coagulation curve data, data in the coagulation reaction stop search interval are used for searching for the coagulation end point. In the search for the coagulation endpoint, as described with reference to FIG. 6A, a point where the change in the transmission light amount decreases is searched.

Figure 6A:
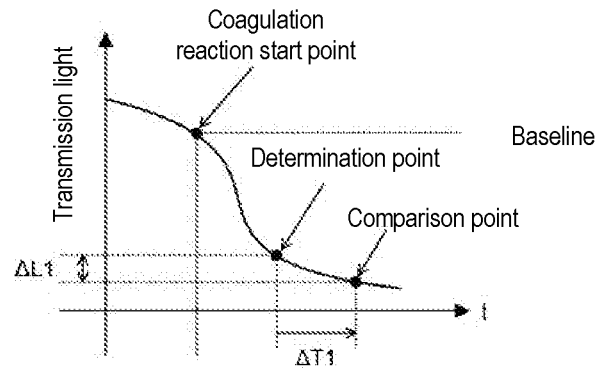
FIG. 6A is a diagram describing a procedure for acquiring a coagulation end point according to the first embodiment.

As shown in FIG. 6A, in the search for the coagulation end point, the processing unit 31 sets a determination point and a comparison point after a time ΔT1 from the determination point on the coagulation curve. When the difference ΔL1 in the amount of transmission light between the determination point and the comparison point is equal to or less than the predetermined threshold value, the processing unit 31 sets the determination point to the coagulation end point.

Figure 6B:
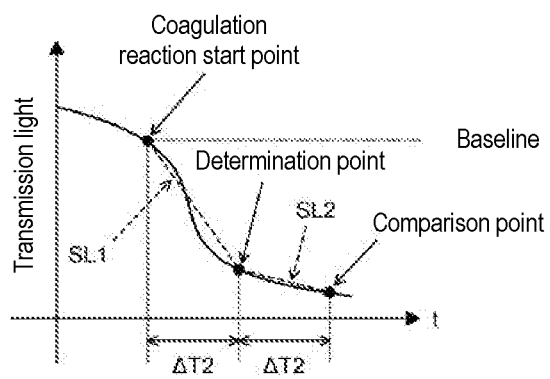
FIGS. 6B and 6C are diagrams describing a procedure of acquiring the coagulation end point according to a modified example.
Figure 6C:
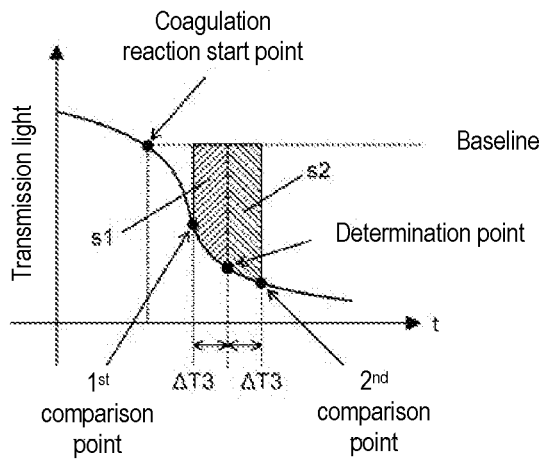

It should be noted that the search for the coagulation endpoint is not limited to the procedure shown in FIG. 6A, and may be the procedure shown in FIG. 6B, or the procedure shown in FIG. 6C.

In the case of the modification shown in FIG. 6B, the processing unit 31 sets a determination point and a comparison point after a time ΔT2 from the determination point on the coagulation curve. The time ΔT2 is equal to the time interval between the coagulation reaction start point and the determination point. Assuming that the slope of the line connecting the coagulation reaction start point and the determination point is SL1, and the slope of the straight line connecting the determination point and the comparison point is SL2, the processing unit 31 determines that the value of SL2/SL1 is smaller than the predetermined threshold value, and this determination point is set as the coagulation end point.

In the case of the modification shown in FIG. 6C, the processing unit 31 sets, on the coagulation curve, a determination point, a first comparison point before the time ΔT3 from the determination point, and a second comparison point after the time ΔT3 from the determination point. The processing unit 31 sets a region surrounded by oblique lines between the base line and the coagulation curve by extending the straight line upward from the determination point, the first comparison point, and the second comparison point to the baseline. When the area of the shaded area on the first comparison point side is s1 and the area of the hatched area on the second comparison point side is s2, the processing unit 31 sets the value of s2/s1 to be smaller than the predetermined threshold value, and this determination point is set as the coagulation endpoint.

In step S23 of FIG. 3, the processing unit 31 acquires the time when the transmission light amount reaches the coagulation detection % as the coagulation time, that is, the prothrombin time, based on the percentage detection method. The prothrombin time is the measurement result obtained based on the first measurement, that is, the measurement result of the measurement item "PT".

Subsequently, in step S24 of FIG. 3, the processing unit 31 executes an acquisition process for information based on the number of platelets. By the process of step S24, the processing unit 31 specifically acquires information on the number of platelets, information relating to the necessity of additional treatment of the blood sample, and information on the necessity of additional processing on the blood sample, and information relating to a second measurement that is different from the first measurement as information based on the platelet count.

Note that when a coagulation endpoint has been acquired before starting step S24, information based on the number of platelets can be obtained in step S24. Therefore, when it is sufficient to acquire only information based on the number of platelets in the process shown in FIG. 3, the process of acquiring the coagulation time in step S23 may be omitted.

Here, the outline of the processing content of step S24 will be described with reference to FIG. 5.

The processing unit 31 sets an interval corresponding to the end stage of the coagulation reaction of the blood sample as an index value acquisition interval. The end stage of the coagulation reaction is not limited to the coagulation endpoint, and may include the point at which the amount of transmission light is substantially the same as the amount of transmitted light detected at the endpoint of coagulation, such as immediately before the coagulation endpoint or at any time after the coagulation endpoint including all the time period during which light can be detected.

In the first embodiment, the processing unit 31 sets the predetermined time range including the timing after the coagulation end point in the index value acquisition interval. In the first embodiment, the start point of the index value acquisition interval is set as the coagulation endpoint, and the time from the start to the end of the index value acquisition interval, that is, the time width of the index value acquisition interval, is set to, for example, 5 seconds. The processing unit 31 connects a point on the coagulation curve at the start point of the index value acquisition interval and a point on the coagulation curve at the endpoint of the index value acquisition interval with a straight line, and calculates the slope of this straight line.

As a result of various verifications, the inventors found that the state of change in optical information at the end of the coagulation reaction differs depending on the number of platelets in the blood sample. Specifically, the inventors found that when the blood sample contains many platelets, the amount of transmitted light slightly increases in the index value acquiring interval corresponding to the end stage of the coagulation reaction. Based on such findings, the inventors found that the state of the number of platelets in the blood sample can be estimated based on the slope of the straight line acquired from the index value obtaining interval.

Note that when the measurement data are based on the amount of scattered light, a general coagulation curve has a second shape obtained by inverting the first shape in the vertical direction. Therefore, by determining the vertical direction, the coagulation time can be acquired in steps S21 to S23 by the same procedure as above, and information based on the number of platelets can be acquired in step S24. In the case of acquiring the coagulation time on the basis of the light absorbance, the coagulation time can be acquired in steps S21 to S23 by the same procedure, and information based on the number of platelets can be acquired in step S24.

Next, with reference to FIG. 7, the process of obtaining information based on the number of platelets in step S24 of FIG. 3 will be described.

In step S101, the processing unit 31 acquires an index value indicating the change state of the optical information based on the optical information of the index value acquisition interval. In the first embodiment, as shown in FIG. 8A, the start point of the index value acquisition interval is set as the coagulation endpoint, and the time width of the index value acquisition interval is set to 5 seconds.

Note that the index value acquisition interval may be set to an interval near the coagulation endpoint. For example, as shown in FIG. 8B, the start point of the index value acquisition interval may be set before the coagulation endpoint, and the endpoint between the index value acquisitions may be set after the coagulation endpoint. As shown in FIG. 8C, the start point and the end point of the index value acquisition interval may be set after the coagulation end point. As shown in FIG. 8D, the start point and the end point of the index value acquisition interval may be set before the coagulation end point. The time width of the index value acquisition interval is not limited to 5 seconds, and may be 1 second or more and 90 seconds or less. As shown in the verification to be described later, the time width of the index value acquisition interval is preferably 5 seconds or more and 10 seconds or less.

The processing unit 31 acquires the rate of change of the transmission light quantity in the index value obtaining interval as the index value. Specifically, the processing unit 31 calculates the slope of the straight line connecting the point on the coagulation curve at the start point of the index value acquisition interval and the point on the coagulation curve at the end point of the index value acquisition interval as the index value.

Note that when the optical information is the transmission light amount as described above, the processing unit 31 also may calculate the change amount of the transmission light amount from the start point to the end point of the index value acquisition interval as the index value. When the optical information is the amount of scattered light, the processing unit 31 calculates the rate of change or the amount of change in the amount of scattered light as an index value, based on the amount of scattered light at the start point and the end point of the index value acquisition interval. When the optical information is light absorbance, and the transmission light amount at the start point of the index value acquisition interval is I1, the transmission light amount at the end point of the index value acquisition interval is I2, and the time width of the index value acquisition interval is $\Delta T$, the processing section 31 calculates the rate of change based on the following expression (1) or the amount of change based on the following expression (2) as an index value.

$$\text{Rate of change} = \{\log 10(I1/I2)\}/\Delta T \quad (1)$$

$$\text{Amount of change} = \log 10(I1/I2) \quad (2)$$

When the rate of change or the amount of change is acquired as the index value in this way, it is possible to easily grasp the state of change of the optical information in the index value acquisition interval.

Note that the index value is not limited to being acquired based on the point on the coagulation curve at the start point of the index value acquisition interval and the point on the coagulation curve at the end point of the index value acquisition interval. For example, when the index value is the rate of change, the index value may be a value obtained by averaging the slopes of the coagulation curves every 0.1 second, and when the index value is the amount of change, the index value may be a value obtained by averaging the amount of change from the start point every second. The index value is not limited to the average of each value, and may be a variance based on each value or an average of the square of each value.

Figures 9A, 9B:
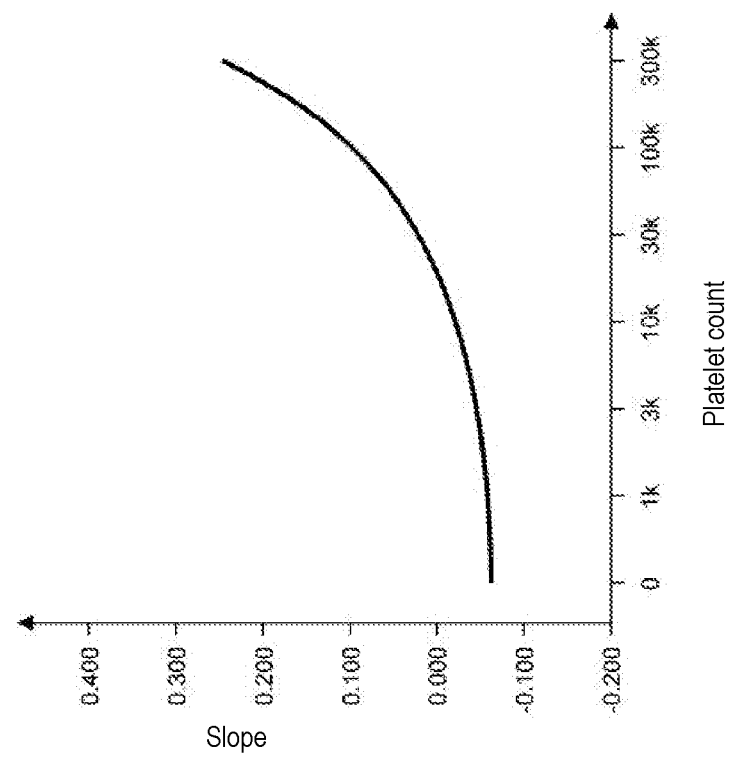
FIG. 9A is a graph showing the correlation between the slope and the number of platelets according to the first embodiment.
FIG. 9B is a table showing the correlation between the slope and the number of platelets according to the first embodiment.

In step S102, the processing unit 31 acquires the number of platelets in the blood sample based on the slope acquired as the index value in step S101 and a table stored in advance in the storage unit 32. According to the verification by the inventors, the larger the value of the slope, the greater the number of platelets in the blood sample, and the correlation between the slope and the number of platelets is as shown in the graph of FIG. 9A. Therefore, if the table as shown in FIG. 9B) representing a point on the curve in FIG. 9A is used as a table showing the correlation between the slope and the number of platelets, the number of platelets can be acquired from the slope. FIG. 9B shows the points on the curve of FIG. 9A at predetermined intervals in a table.

In step S102, the processing unit 31 obtains the number of platelets by referring to the table shown in FIG. 9B based on the slope acquired in step S101. The platelet count of the table is, for example, the number of platelets contained per 1 µL. Note that when the slope acquired in step S101 is between the first slope and the second slope in the table of FIG. 9B, the processing unit 31 calculates a value between the number of platelets corresponding to the first slope and the number of platelets corresponding to the second slope as the number of platelets by calculation. When the number of platelets is acquired as information based on the number of platelets, the operator can grasp how many platelets are contained in the blood sample, and can directly determine the influence of the number of platelets on the measurement result.

Note that instead of storing a table in the storage unit 32, an expression representing the graph shown in FIG. 9A may be stored. In this case, the processing unit 31 calculates the number of platelets from the slope acquired in step S101 and the expression representing the graph shown in FIG. 9A.

In step S103, the processing unit 31 compares the platelet count acquired in step S102 with a plurality of threshold values. The threshold value compared in step S103 corresponds to the second reference value. The plurality of threshold values are, for example, 10,000 platelets/μL, 30,000 platelets/μL, 50,000 platelets/μL. These thresholds are threshold values used for determining the number of platelets contained in the blood sample. In particular, 10,000 platelets/μL is the boundary value of the number of platelets necessary for suppressing the influence on the measurement result described in the Journal of the Japan Society of Laboratory Hematology, vol. 17, No. 2, "Consensus on Coagulation Test Sample Handling". That is, when the number of platelets is less than 10,000 platelets/μL, it is understood that the influence of platelets on the measurement result is minimal. Note that the threshold value to be compared with the number of platelets may be one, for example, only 10,000 platelets/μL may be used.

In step S104, based on the comparison result of step S103, the processing unit 31 stores information on the influence on the second measurement and information on the necessity of additional treatment of the blood sample as information based on the number of platelets. In other words, the information acquired here is information based on the level of the number of platelets in the blood sample, and the information relating to the influence on the second measurement suggests the existence of measurement items affected by the platelets in the blood sample. When information based on the level of the number of platelets in the blood sample is acquired, the operator can determine whether the number of platelets in the blood sample exceeds each threshold by referring to this information.

Here, the second measurement is a measurement different from the first measurement which is the measurement relating to the measurement item "PT". Platelets contained in blood sample are less likely to affect the measurement results of the first measurement, but may adversely affect the measurement results of the second measurement. Examples of measurement items of the first measurement are "PT" and "Fbg". Examples of measurement items of the second measurement include "lupus anticoagulant (LA)", "coagulation factor XIII", "pai-1", and the like. In this way when the number of platelets in the blood sample is large, even if the measurement result of the first measurement is appropriate, the measurement result of the second measurement may be inappropriate in some cases. In such a case, if information relating to the influence on the second measurement is acquired as information based on the number of platelets, the operator can determine whether the measurement result of the second measurement is appropriate.

The additional treatment of the blood sample is an additional treatment for obtaining an appropriate blood sample. For example, additional treatment of a blood sample includes a process of re-obtaining the blood sample by centrifuging the blood sample of the subject that has already been acquired, a process of collecting the whole blood specimen again from the subject, and a process of centrifuging the whole blood sample to reacquire the blood sample. When information on the necessity of additional treatment is acquired as information based on the number of platelets, the operator can determine whether it is necessary to reacquire the blood sample in a proper state.

In step S105, the processing unit 31 causes the display unit 33 to display information based on the number of platelets in accordance with the display instruction input by the operator via the input unit 34. In this way the operator can visually grasp information based on the number of platelets in the blood sample. In this way, the acquisition process of information based on the number of platelets is completed.

Next, with reference to FIGS. 10 to 12, the screens 110, 120, and 130 displayed on the display unit 33 in step S105 in FIG. 7 will be described.

As shown in FIG. 10, the screen 110 includes a list 111 and a detail display button 112.

The list 111 displays information on each blood sample. The display items of the list 111 include a state, a sample number, an end time, a start time, a date, and measurement result for each measurement item.

Figure 7:
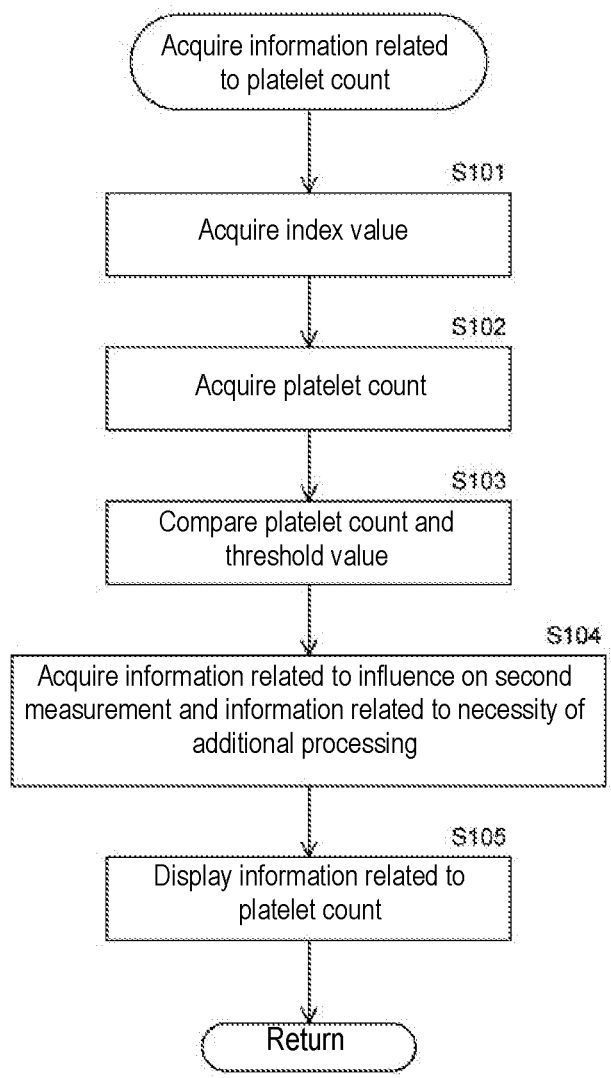
FIG. 7 is a flowchart showing information an acquisition process based on the number of platelets according to the first embodiment.

In the processes shown in FIGS. 3 and 7, the blood analyzer 10 performs only the first measurement, acquires the coagulation time, that is, the measurement result of the measurement item "PT" based on first measurement, and acquires information based on the platelet count. However, when a measurement order including measurement items other than the measurement item "PT" is set for one blood sample, the blood analyzer 10 performs measurements other than the first measurement according to the measurement order, and acquires measurement results based on the other measurements. Measurement items of other measurements include fibrinogen (Fbg), activated partial thromboplastin time (APTT), lupus anticoagulant (LA), coagulation factor XIII, pai-1 and the like.

As shown in FIG. 10, one row extending in the lateral direction of the list 111 corresponds to one blood sample. In the example shown in FIG. 10, the measurement results of the measurement items "PT", "Fib", and "LA" are displayed for each blood sample. Note that the list 111 is provided with a scroll bar extending in the vertical direction for displaying all blood samples and a scroll bar extending in the left and right direction for displaying all measurement results.

For example, "Review" is displayed in the display item of the state. "Review" indicates that there is a possibility that the platelet count is high for the corresponding blood sample. In the example shown in FIG. 10, as a result of comparison between the platelet number and the threshold in the sample numbers "0002" and "0004" in step S103 of FIG. 7, "Review" is displayed in the display item of the state since the blood sample contains platelets of 10,000 platelets/μL or more. As described above, it is determined that there is an influence on the second measurement and determined there is a necessity for additional treatment to acquire a proper blood sample in step S104 of FIG. 7 for blood samples that display "Review" that are determined to contain more than 10,000 platelets/μL. That is, the display of "Review" is information on the influence on the second measurement, and is information on the necessity of additional treatment.

When "Review" is displayed in this manner, numerical values are displayed as measurement results in measurement items other than measurement items related to the second measurement, for example, measurement items "PT" and "Fib" which can be the first measurement, "*" and "- -" indicating that the measurement result is masked are displayed in the measurement items related to the second measurement. This mask display is also information on the influence on the second measurement, and is information on the necessity of additional processing. Note that in the measurement items related to the second measurement, numerical values may be displayed in the measurement result together with "*" indicating that the measurement result needs to be masked.

When confirming the detailed information on the blood sample, the operator selects the row of the corresponding blood sample in the list 111 via the input unit 34. In this way a frame 111a is added to the row of the corresponding blood sample. Then, the operator operates the detail display button 112 via the input unit 34. In this way the processing unit 31 causes the display unit 33 to display a screen 120 including detailed information on the selected blood sample.

Figure 11:
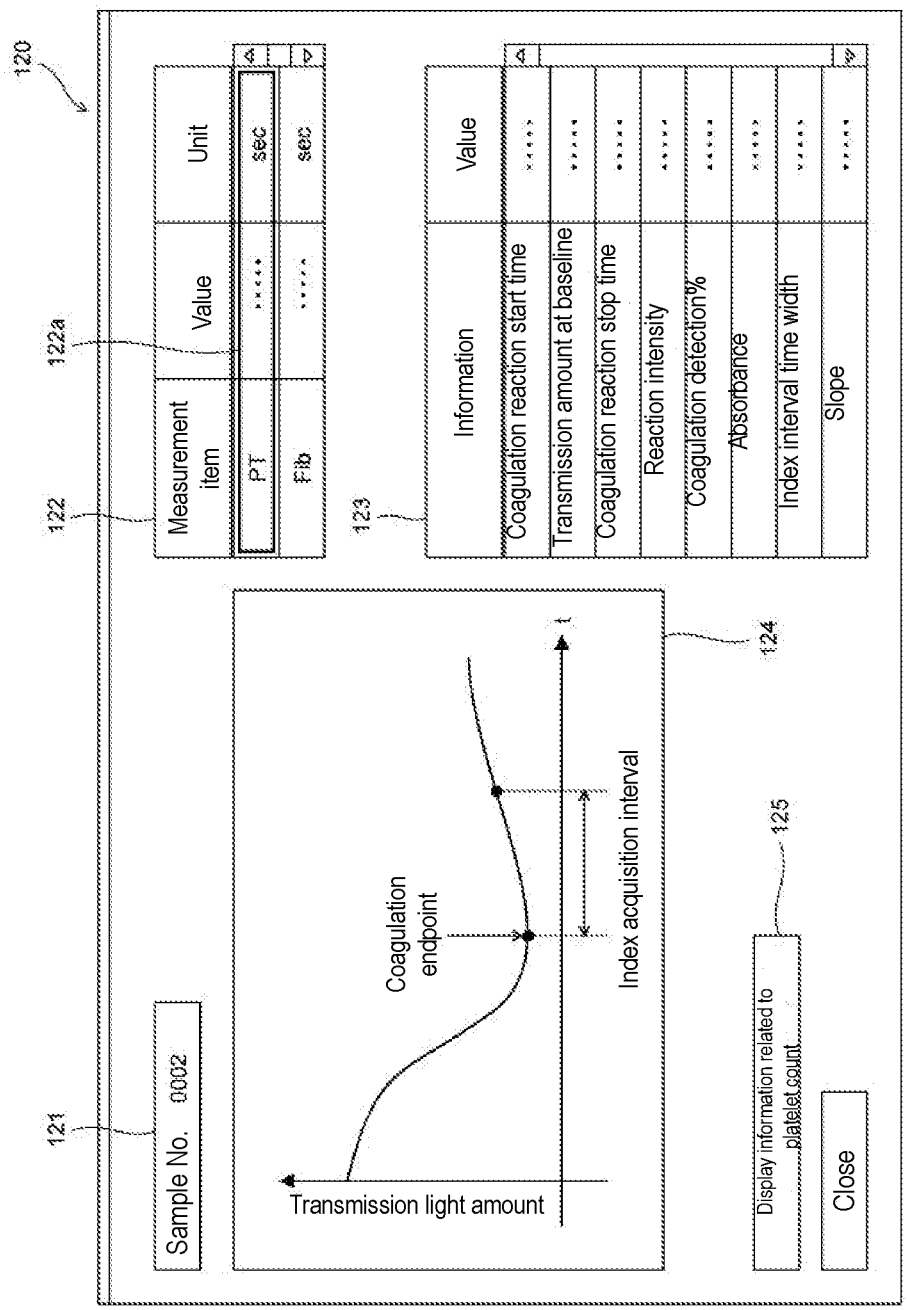
FIG. 11 is a diagram schematically showing a configuration of a screen displayed on a display unit according to the first embodiment.

As shown in FIG. 11, the screen 120 includes a sample number display area 121, lists 122 and 123, a graph display area 124, and a display button 125.

The sample number display area 121 displays the sample number of the blood sample displayed on the screen 120. The list 122 displays the measurement results of all the measurement items performed on the blood sample displayed on the screen 120. The list 122 is provided with a scroll bar extending in the vertical direction so that all measurement results can be displayed. The operator selects the row of the corresponding measurement item in the list 122 when displaying the detailed information on the measurement result. In this way a frame 122a is attached to the line of the corresponding measurement item. When the line of the measurement item of the list 122 is selected, the list 123 and the graph display area 124 displays detailed information on the corresponding measurement item.

The list 123 displays detailed numerical information on the measurement item selected in the list 122. Since "PT" is selected as the measurement item in the example shown in FIG. 11, the display items of the list 111 include coagulation reaction start time, transmission light amount at baseline, coagulation reaction stop time, reaction intensity, coagulation detection %, absorbance, time width of the index value acquisition interval, and slope.

The coagulation reaction start time is the time at the coagulation reaction start point. The coagulation reaction stop time is the time at the coagulation endpoint. The reaction intensity is obtained by subtracting the transmission light amount at the endpoint of coagulation from the transmission light amount at the baseline. The light absorbance is a value corresponding to the turbidity of the blood sample, and is calculated based on the transmission light amount at the baseline and the transmission light amount at the coagulation endpoint. The time width of the index value acquisition interval is a value used when acquiring the index value in step S101 of FIG. 7. The slope is the index value acquired in step S101 of FIG. 7. Note that a separate input screen also may be provided so that the operator can set the time width of the index value acquisition interval.

The graph display area 124 displays a graph obtained by measurement on the measurement item selected in the list 122. In the example shown in FIG. 11, since "PT" is selected as the measurement item, the coagulation curve obtained by the first measurement on the measurement item "PT" is displayed in the graph display area 124.

The display button 125 is a button for displaying information based on the platelet count. The operator operates the display button 125 via the input unit 34 when displaying information based on the platelet count for the blood sample displayed on the screen 120. In this way the processing unit 31 causes the display unit 33 to display the screen 130 including the information based on the platelet count.

Figure 12:
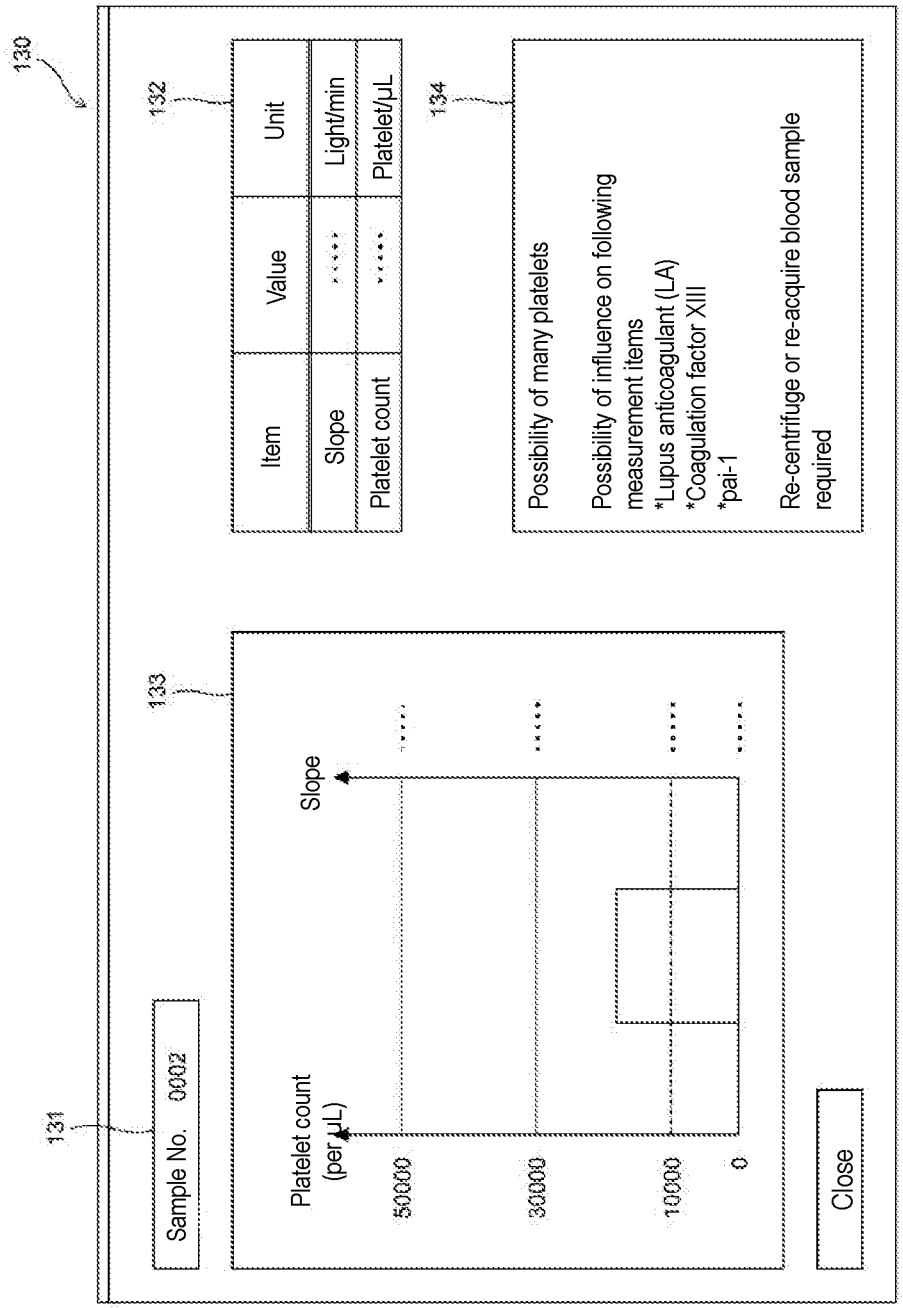
FIG. 12 is a diagram schematically showing a configuration of a screen displayed on a display unit according to the first embodiment.

As shown in FIG. 12, the screen 130 includes a sample number display area 131, a list 132, a graph display area 133, and a comment area 134.

The sample number display area 121 displays the sample number of the blood sample displayed on the screen 130. The list 132 displays the slope and the platelet count obtained based on the blood sample displayed on the screen 120. The graph display area 133 displays a graph showing the results of comparing the slope and the platelet count displayed in the list 132 with a threshold value. The graph display area 133 shows three threshold values compared to the slope and three threshold values compared to the platelet count. Among these thresholds, the threshold indicated by the lowermost dashed line is the threshold corresponding to the number of platelets of 10,000/μL. The display content of the graph display area 133 is also information based on the level of the platelet count in the blood sample. A separate input screen also may be provided so that the operator can set three threshold values related to the slope and the platelet count.

The comment area 134 displays information on the influence on the second measurement and information on the necessity for additional processing. In the example shown in FIG. 12, since the platelet count is 10,000/μL or more, "the possibility of having many platelets" is displayed in the comment area 134. Since there is a possibility that there are many platelets, the possibility that the second measurement may be affected is displayed in the comment area 134, and the measurement item of the second measurement which may be influenced is specified. In the comment area 134, "the measurement result of the second measurement may be inappropriate" also may be displayed. In addition, as "requirement of blood sample to be re-centrifuged or re-acquired" is displayed as information on the necessity of additional processing.

Next, a test flow performed by the operator using the above-described blood analysis process will be described.

Figure 13:
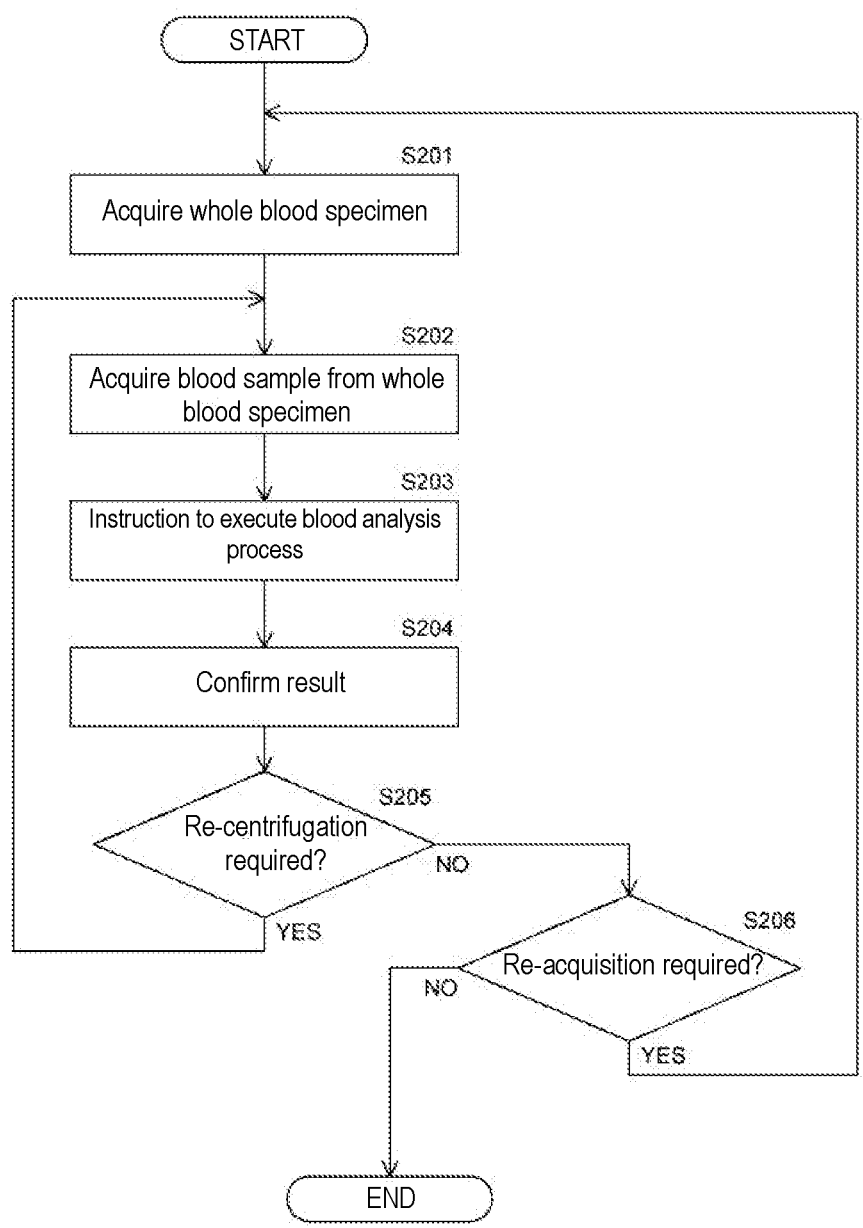
FIG. 13 is a flowchart showing an examination procedure performed by an operator according to the first embodiment.
Figure 14:
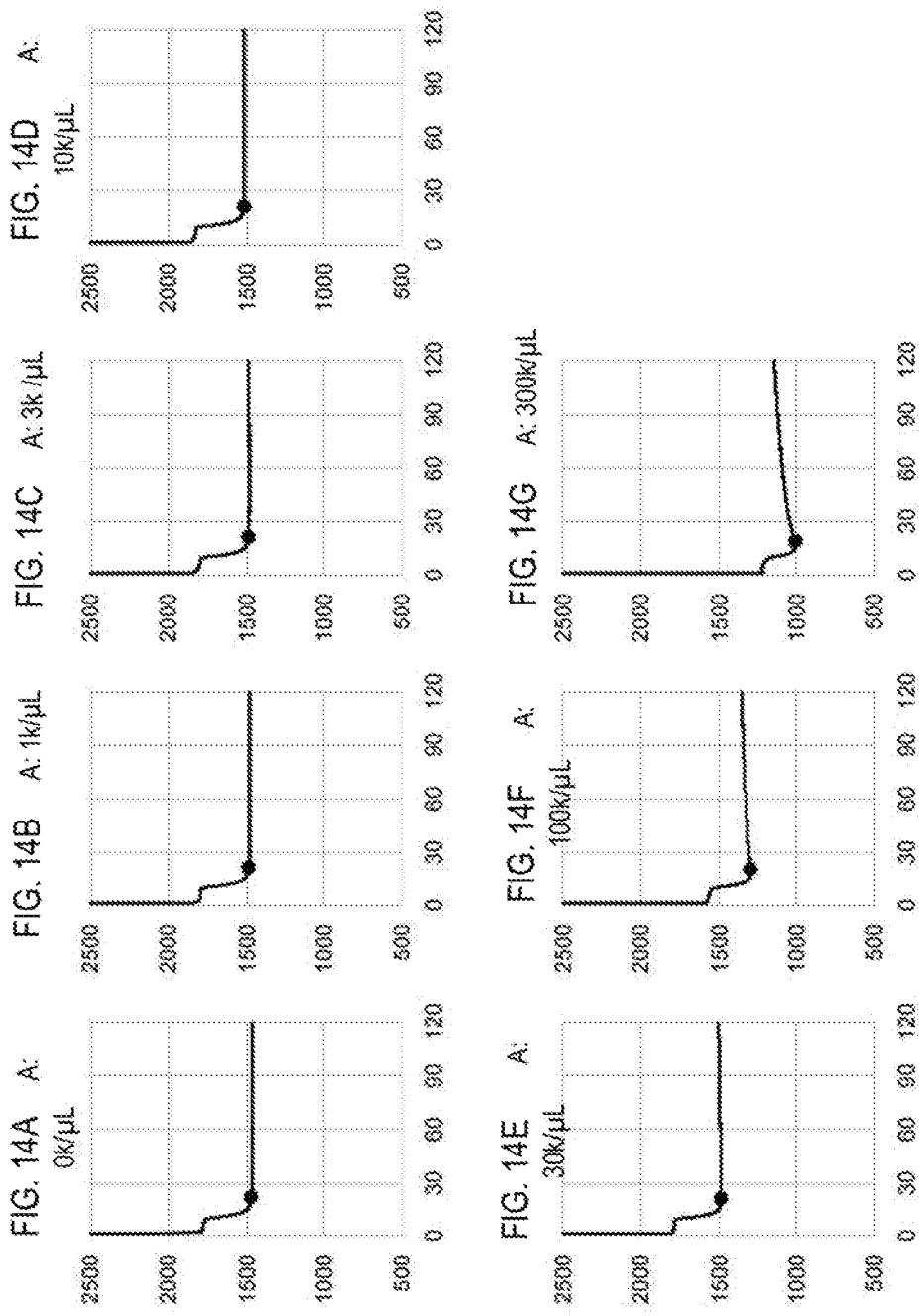
FIGS. 14A to 14G are diagrams showing coagulation curves acquired in the verification according to the first embodiment.
Figure 15:
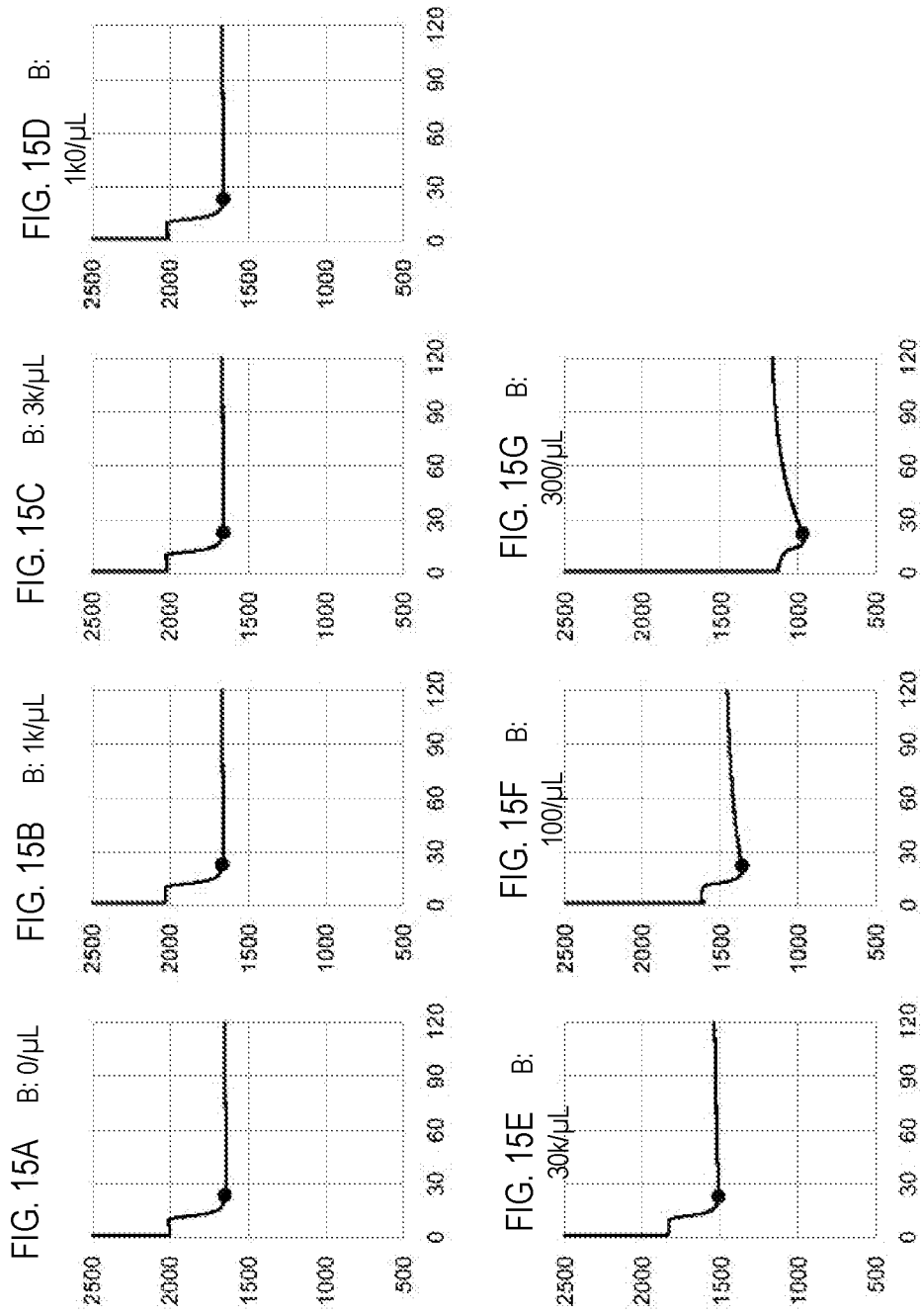
FIGS. 15A to 15G are diagrams showing coagulation curves acquired in the verification according to the first embodiment.
Figure 16:
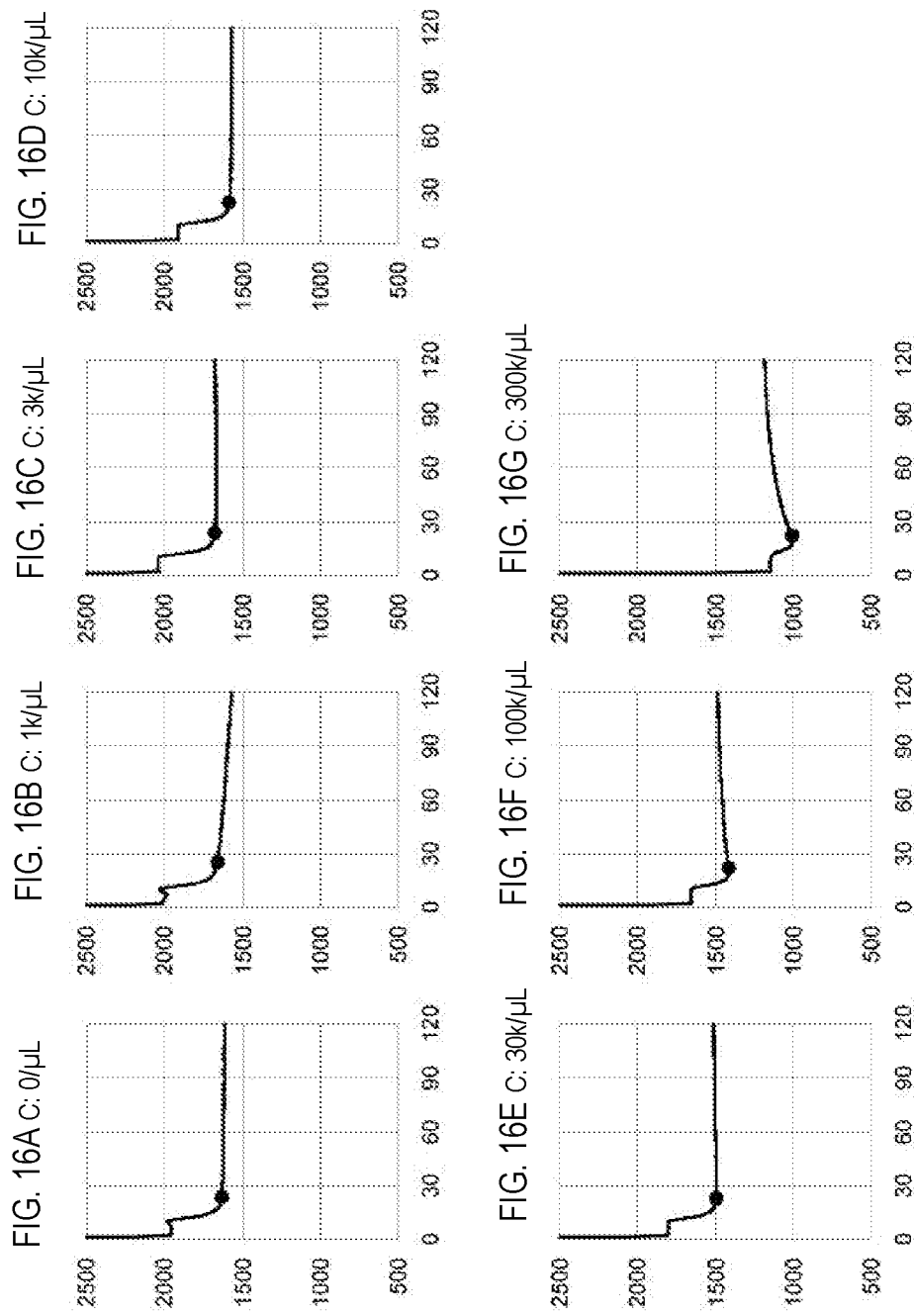
FIGS. 16A to 16G are diagrams showing coagulation curves acquired in the verification according to the first embodiment.

As shown in FIG. 13, in step S201, the operator acquires a whole blood sample from the subject. In step S202, the operator obtains a blood sample from the whole blood specimen. Specifically, the operator centrifuges the whole blood specimen using a centrifuge to obtain plasma as a blood sample. In step S203, the operator uses the input unit 34 of the blood analyzer 10 to input an instruction for performing the blood analysis process shown in FIGS. 3 and 7. In this way the processes of FIGS. 3 and 7 are performed based on the blood sample.

In step S204, the operator confirms the display contents of the screens 110, 120, and 130 displayed in step S105 of FIG. 7, and checks information on platelet count, information on the need for additional processing of the blood sample, and information on the influence on the second measurement. Based on the content confirmed in step S204, the operator determines whether additional processing relating to the blood sample, that is, re-centrifugation of the blood sample or reacquisition of the whole blood sample is necessary.

If the operator determines that the blood sample needs to be re-centrifuged, the determination result in step S205 is YES, and the process is returned to step S202. In step S202, the operator again performs centrifugation on the blood specimen already acquired in step S201, and reacquires the blood sample. Then, the operator performs the process after step S203. When the operator determines that it is necessary to reacquire the whole blood specimen, the determination result in step S206 is YES, and the process is returned to step S201. The operator acquires the whole blood specimen again from the subject in step S201. Then, the operator reacquires the blood sample in step S202, and performs the process of step S203 and subsequent steps. If the operator determines that re-centrifugation and re-acquisition is not necessary, the process of FIG. 13 ends.

As described above, when the operator confirms the content displayed in step S105 of FIG. 7 and determines that there is a need for additional processing relating to the blood sample based on the display content, re-centrifugation of the blood sample or whole blood is performed and to reacquire the blood sample. This allows the test to proceed smoothly and properly.

Verification

Next, verification performed by the inventors will be described. The inventors used the blood coagulation analyzer "CS-5100" manufactured by Sysmex Corporation to measure and analyze the measurement item "PT" based on a blood sample prepared in advance to include a predetermined number of platelets.

In the preparation of blood samples, the inventors collected whole blood specimens from healthy persons A to C, respectively, and prepared seven blood samples with different platelet counts from each whole blood specimen. At this time, the inventors acquired blood samples containing platelet counts of approximately zero for sufficient centrifugation, and acquired blood samples containing a certain number of platelets that were to be subjected to insufficient centrifugation from the whole blood specimens. Then, the inventors measured a blood sample containing a certain number of platelets using CS-5100 to obtain a platelet count, that is, a concentration of platelets.

The present inventors prepared seven types of blood samples containing a predetermined number of platelets from a single whole blood specimen by mixing the blood sample made the platelet count almost zero processing via sufficient centrifugation relative to the blood samples that acquired a platelet concentration. The seven types of prepared blood samples contained 0 platelets/µL, 1,000 platelets/µL, 3,000 platelets/µL, 10,000 platelets/µL, 30,000 platelets/µL, 100,000 platelets/µL, and 300,000 platelets/µL, respectively. Thus, the inventors obtained blood samples of seven different concentrations from one whole blood sample.

Next, using the blood coagulation analyzer, the measurement item "PT" was measured for a total of 21 types of blood samples to acquire the coagulation curves shown in FIG. 14A to FIG. 16G. In PT measurement, Thromborel S manufactured by Sysmex Corporation was used as a reagent for measuring coagulation time. FIGS. 14A to 14G show coagulation curves of seven types of blood samples prepared from healthy person A. Similarly, FIGS. 15A to 15G show coagulation curves of seven types of blood samples prepared from healthy person B. FIGS. 16A to 16G show coagulation curves of seven types of blood samples prepared from healthy person C. In the graphs of FIG. 14A to FIG. 16Q the horizontal axis indicates the elapsed time, and the vertical axis indicates the transmitted light amount. Solid circles in the coagulation curve indicate the coagulation endpoint.

From the results of FIG. 14A to FIG. 16Q it is understood that the gradient near the coagulation endpoint increases as the number of platelets contained in the blood sample increases in any of the healthy persons A to C. Therefore, it can be said that information based on the number of platelets in a blood sample can be acquired based on optical information of the index value acquisition period near the coagulation end point.

Note that when the blood sample contains a predetermined number of platelets, the phenomenon that the amount of transmitted light increases again after the coagulation endpoint, that is, the phenomenon that the light absorbance decreases after the coagulation endpoint, is believed to be due to platelet activation.

Figure 17:
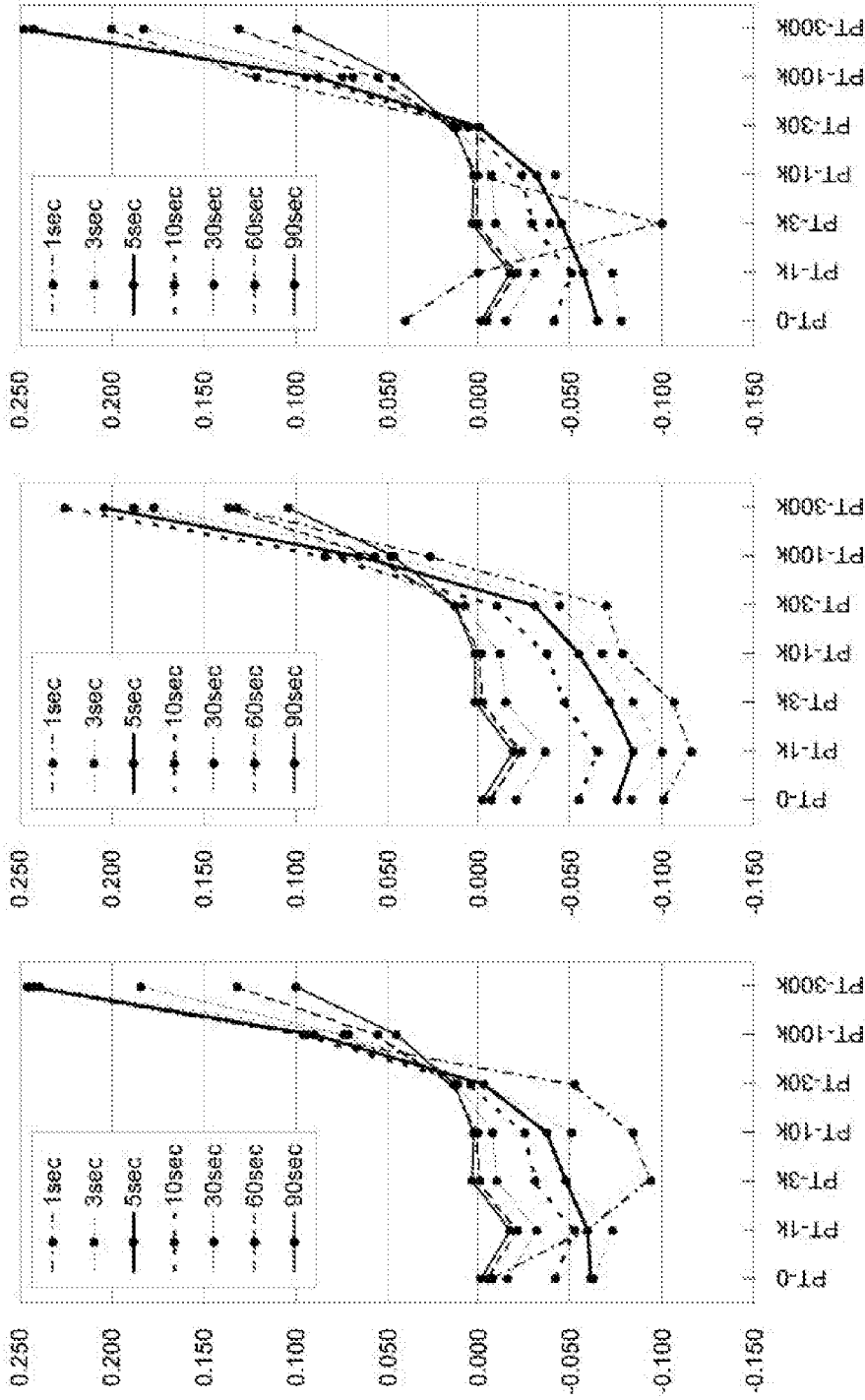
FIGS. 17A to 17C are diagrams showing verification results in which the slope changes in accordance with the number of platelets according to the first embodiment.

FIG. 17A, is a graph showing the value of the slope acquired by a procedure similar to the first embodiment performed based on the 21 types of blood samples when the start point of the index value acquisition interval is the coagulation endpoint, and the time width of the index value acquisition interval is changed. The seven broken lines on the graph indicate the slopes when the time width of the index value acquisition interval is 1 second, 3 seconds, 5 seconds, 10 seconds, 30 seconds, 60 seconds, and 90 seconds. The horizontal axis direction of the graph blood samples including platelet counts of 0/µL, 1,000/µL, 1,000/µL, 10,000/µL, 30,000/µL, 100,000/µL, 300,000/µL. The vertical axis direction of the graph indicates the value of the acquired slope. Three types of blood samples containing a predetermined number of platelets were prepared based on healthy persons A to C, and the black circles on the graph are obtained by averaging the slopes obtained from three types of blood samples containing the same number of platelets.

As shown in FIG. 17A, it was found that the slope generally increases as the number of platelets contained in the blood sample increases in the time width of any index value acquisition interval. Therefore, it can be said that the number of platelets contained in the blood sample can be estimated according to the slope obtained when the start point of the index value acquisition interval is taken as the coagulation endpoint. In addition, when the time width of the index value acquisition interval is 5 seconds and 10 seconds, the slope substantially monotonically increases with the increase in the platelet count, and the difference in slope was large when platelet count was 1,000/µL and when platelet count was 300,000/µL. Therefore, if the time width of the index value acquisition interval is set to 5 seconds or more and 10 seconds or less, the resolution in the vertical axis direction is enhanced, so it can be said that the number of platelets contained in the blood sample can be accurately estimated.

Note that although a table showing the correlation between the slope and the number of platelets is used in the first embodiment as shown in FIG. 9B, the graph shown in FIG. 9A which is the source of this table of FIG. 9B is based on the graph when the time width of the index value acquisition interval is 5 second (FIG. 17A).

FIG. 17B is a graph showing the value of the slope acquired by a procedure similar to that of the first embodiment based on the 21 types of blood samples when the start point of the index value acquisition interval is 3 seconds before the coagulation endpoint and the time width of the index value acquisition interval is changed. In this case, it was found that the slope generally increases as the number of platelets contained in the blood sample increases in the time width of any index value acquisition interval. Therefore, it can be said that the number of platelets contained in the blood sample can be estimated according to the slope obtained when the start point of the index value acquisition interval is 3 seconds before the coagulation endpoint. If the time width of the index value acquisition interval is set to 5 seconds or more and 10 seconds or less, it can be said that the number of platelets contained in the blood sample can be accurately estimated for the same reason as in the case of FIG. 17A.

FIG. 17C is a graph showing the value of the slope acquired by a procedure similar to first embodiment based on the 21 types of blood samples when the start point of the index value acquisition section is 0.5 seconds after the coagulation endpoint and the time width of the index value acquisition interval is changed. Also in this case, it was found that the slope generally increases as the number of platelets contained in the blood sample increases in the time width of any index value acquisition interval. Therefore, it can be said that the number of platelets included in the blood sample can be estimated according to the slope acquired when the start point of the index value acquisition interval is 0.5 seconds after the coagulation endpoint. If the time width of the index value acquisition interval is set to 5 seconds or more and 10 seconds or less, it can be said that the number of platelets contained in the blood sample can be accurately estimated for the same reason as in the case of FIG. 17A.

The inventors also measured the measurement item "Fbg" for a total of seven types of blood samples using the blood coagulation analyzer, and acquired the coagulation curves shown in FIGS. 18A to 18G. In Fbg measurement, Thrombocheck Fib (L) manufactured by Sysmex Corporation was used as a reagent for measuring coagulation time. The blood sample in this case is a blood sample set to seven different concentrations, as in the above-described verification of the measurement item "PT".

Figure 18:
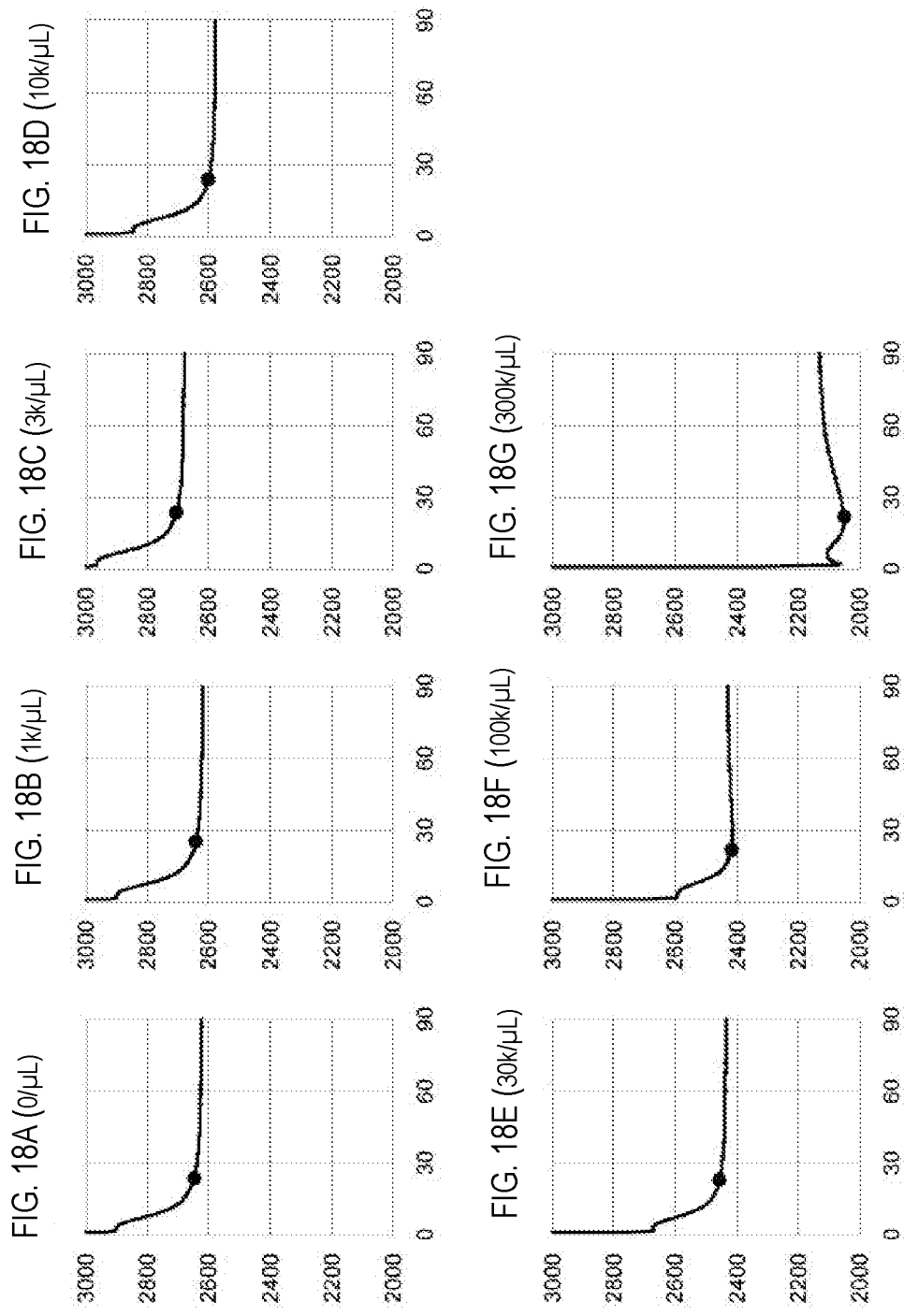
FIGS. 18A to 18G are diagrams showing coagulation curves acquired in verification according to a modification.

From the results of FIGS. 18A to 18Q it was found that in the case of the measurement item "Fbg", the slope after the coagulation endpoint gradually increases as the number of platelets contained in the blood sample increases. Therefore, it can be said that the information based on the platelet count can be acquired as in the first embodiment based on the optical information acquired by the measurement of the measurement item "Fbg".

Second Embodiment

Figure 19:
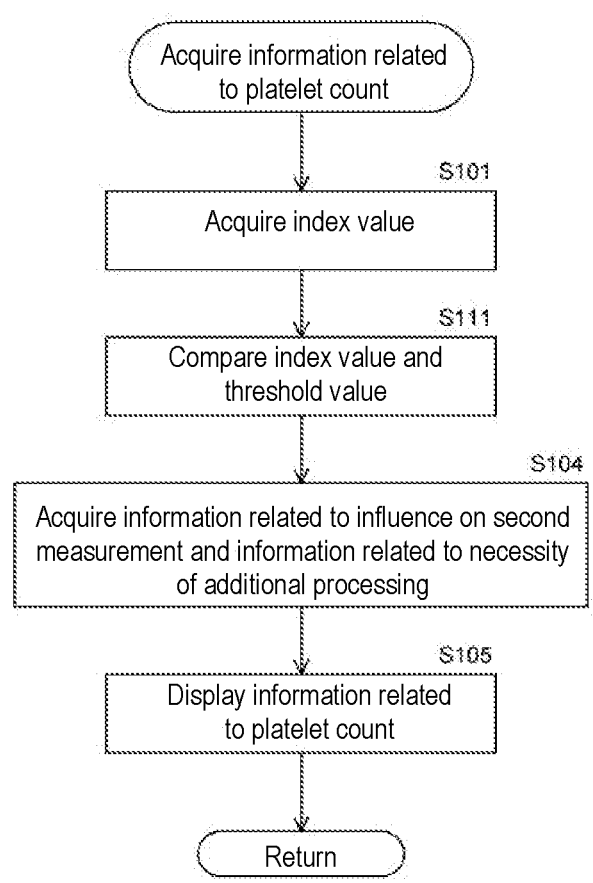
FIG. 19 is a flowchart showing an information acquiring processing based on the number of platelets according to a second embodiment.

In the second embodiment, processing for acquiring information based on the number of platelets was performed as shown in FIG. 19. In the process of FIG. 19, step S102 is omitted and step S111 is added instead of step S103 as compared with the process of the first embodiment shown in FIG. 7. In the second embodiment, the table shown in FIG. 9B showing the correlation between the slope and the number of platelets is not used since step S102 is omitted. The other processes and configurations of the second embodiment are similar to those of the first embodiment.

In step S111, the processing unit 31 compares the index value acquired in step S101, that is, the slope, with a plurality of threshold values. The plurality of threshold values are, for example, slope values corresponding to platelet counts of 10,000/µL, 30,000/µL, and 50,000/µL. The threshold value compared in step S111 corresponds to the first reference value. Then, in step S104, as in the first embodiment, the processing unit 31 acquires information relating to the influence on the second measurement and information on the necessity of additional treatment of the blood sample as information based on the platelet count on the basis of the comparison result of step S103. The information acquired in this case is information based on the level of the number of platelets in the blood sample, as in the first embodiment.

In step S105, the processing unit 31 causes the display unit 33 to display information based on the platelet count. Also in the second embodiment, the screens 110, 120, and 130 are displayed on the display unit 33 as in the first embodiment. However, in the second embodiment, since the platelet count is not acquired, the display of the platelet count in the list 132 is omitted on the screen 130 shown in FIG. 12.

The index value, that is, the slope, reflects optical information of the index value acquisition interval, and changes in accordance with the number of platelets in the blood sample. Therefore, it is possible to obtain information on the influence on the second measurement directly from the index value and information on the necessity of additional processing of the blood sample without obtaining the platelet count from the index value. In this way the operator can determine whether the number of platelets in the blood sample has exceeded the reference value by referring to the information based on the level of the number of platelets in the blood sample in the second embodiment.

Third Embodiment

Figure 20:
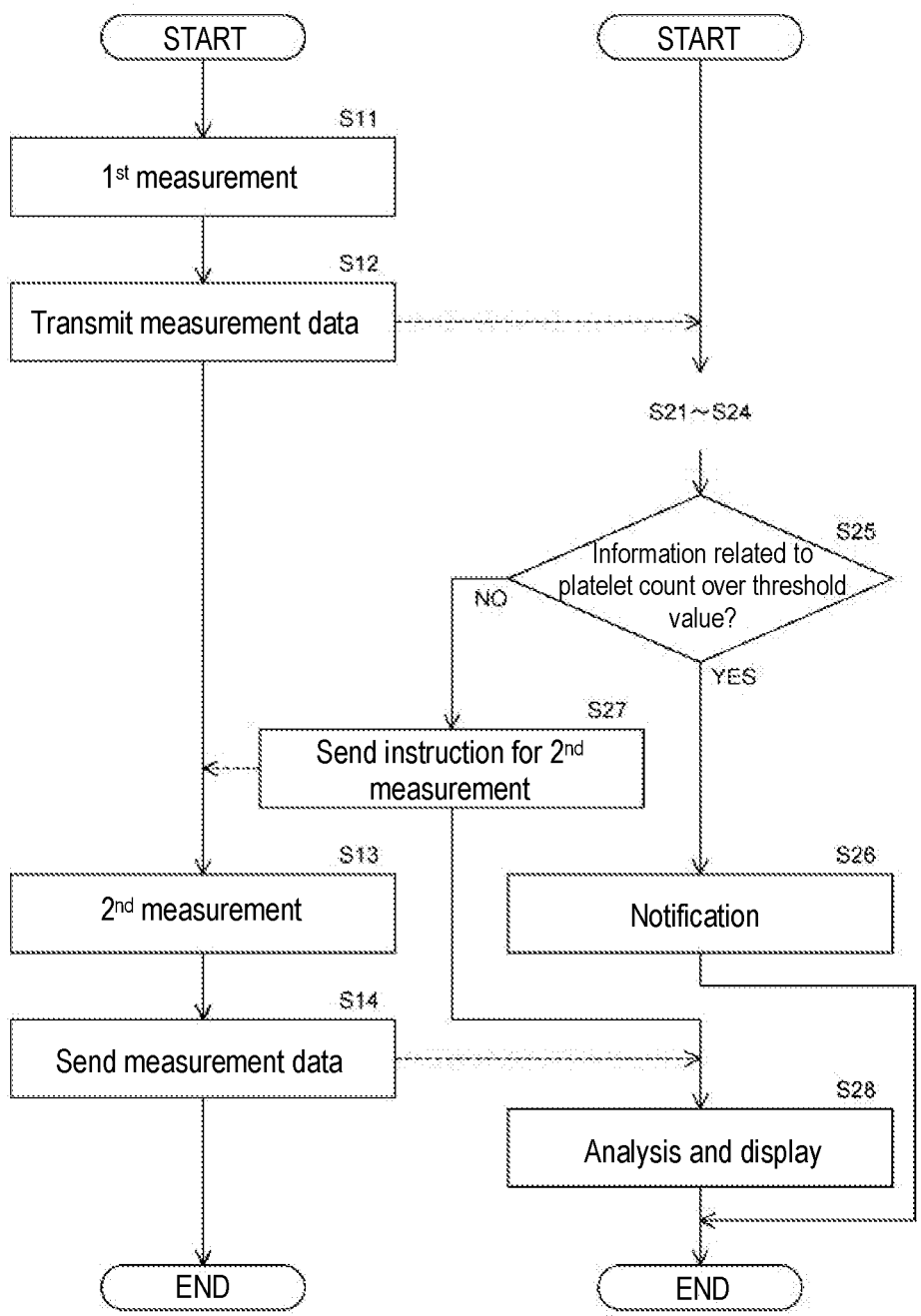
FIG. 20 is a flowchart showing a blood analysis method according to a third embodiment.

In the third embodiment, when a measurement order including the measurement items of the first measurement and the second measurement is set for one blood sample, the second measurement and the notification to the operator are performed according to the information based on the platelet count as shown in FIG. 20. In the process of FIG. 20, steps S13 and S14 are added after step S12, and steps S25 to S28 are added after the step S24, as compared with the process of the first embodiment shown in FIG. 3. Also in the third embodiment, the first measurement is a measurement of measurement items such as PT and Fbg, which are less affected by the platelet count, and the second measurement is measurement of measurement items that are more influenced by platelet count such as fibrinogen (Fbg), activated partial thromboplastin time (APTT), lupus anticoagulant (LA), coagulation factor XIII, pai-1. The other processes and configurations of the third embodiment are the same as those of the first embodiment.

In step S25, the processing unit 31 determines whether the information based on the platelet count acquired in step S24 is equal to or more than a predetermined threshold value. Specifically, the processing unit 31 determines whether the platelet count or the index value acquired in step S24 is equal to or more than a predetermined threshold value. If the information based on the platelet count is equal to or more than the predetermined threshold value, the processing unit 31 transmits an instruction of the second measurement to the measuring device 20 because an appropriate measurement result can not be obtained even if the second measurement is performed, and the second measurement is not performed. As described above, when the second measurement is not performed, it is possible to prevent the second measurement from being performed based on an inadequate blood sample having many platelets.

In this case, in step S26, the processing unit 31 performs a process of issuing notification information indicating that the second measurement is affected, and a process of notification information about the necessity of the additional process regarding the blood sample before the second measurement. In the third embodiment, the information indicating that the second measurement is affected and the information about the necessity of the additional processing are not displayed in step S105 of FIG. 7, and these notifications are performed in step S26 when the information based on the platelet count is equal to or greater than a predetermined threshold value. Thus, when the information indicating that there is an influence on the second measurement is issued, the operator can understand that there is an influence on the second measurement. When information on the necessity of additional treatment of the blood sample before the second measurement is generated, the operator can grasp the necessity of additional processing.

Note that the notification is performed by display on the display unit 33 as shown in FIG. 12. However, the embodiment is not limited to this, inasmuch as the notification may be performed via voice. In addition, at least one notification of information indicating that the second measurement is not performed, an indication that the second measurement is affected, and information on the necessity of additional processing for the blood sample may be performed.

On the other hand, when the information based on the platelet count is less than the predetermined threshold value, the processing unit 31 transmits an instruction of the second measurement to the measurement device 20 in step S27. When receiving the second measurement instruction, the measuring device 20 prepares a blood sample for the second measurement based on the blood sample in step S13, and performs the second measurement. In step S14, the measurement device 20 transmits the measurement data acquired in step S13 to the control device 30.

In step S28, the processing unit 31 analyzes the measurement item related to the second measurement based on the measurement data transmitted from the measurement device 20 in step S14, and displays the measurement result related to the second measurement on the display unit 33. As described above, since the second measurement is performed only when it is determined from the first measurement that the platelet count is low, a measurement result of an appropriate second measurement can be obtained.

What is claimed is:

1. A blood analysis method comprising:
   acquiring optical information which changes over time from a mixed liquid of a blood sample and a reagent for coagulation time measurement after mixing the blood sample and the reagent; and
   acquiring information related to a coagulation time and information related to a number of platelets in the blood sample based on the acquired optical information,
   wherein the optical information comprises an intensity of transmission light, an intensity of scattered light or light absorbance,
   the information related to the coagulation time comprises the coagulation time or a concentration obtained based on the coagulation time, and
   the information related to the number of platelets comprises a number of platelets, information regarding a necessity of additional treatment on the blood sample, or a level of platelet count, and
   wherein the information related to the number of platelets in the blood sample is acquired based on the optical information in a predetermined time range including a timing after a coagulation end point.

2. The blood analysis method according to claim 1, wherein an end stage of a coagulation reaction of the blood sample is set at the coagulation end point of the blood sample in the acquired optical information of the blood sample mixed with the coagulation time measurement reagent, immediately before the coagulation end point, or any time after the coagulation end point.

3. The blood analysis method according to claim 1, further comprising
   detecting the coagulation end point from the acquired optical information.

4. The blood analysis method according to claim 3, further comprising
   acquiring an index value indicating a change of the optical information based on the optical information in the predetermined time range; and
   the information related to the number of platelets in the blood sample is acquired based on the index value.

5. The blood analysis method according to claim 4, wherein the index value is a change rate or a change amount of the optical information within the predetermined time range.

6. The blood analysis method according to claim 5, wherein the change rate or the change amount of the optical information is acquired based on the optical information at a start point and an end point of the predetermined time range.

7. The blood analysis method according to claim 4, wherein information based on a level of the number of platelets in the blood sample is acquired as the information related to the number of platelets in the blood sample by comparing the index value with one or more preset first reference values.

8. The blood analysis method according to claim 4, wherein a platelet count in the blood sample is acquired as the information related to the number of platelets in the blood sample based on the index value.

9. The blood analysis method according to claim 8, wherein information indicating a correlation between the index value and the platelet count is used to obtain the platelet count in the blood sample from the index value.

10. The blood analysis method according to claim 8, further comprising:
    acquiring information related to level of the platelet count in the blood sample as the information related to the number of platelets in the blood sample by comparing the platelet count in the blood sample with one or more preset second reference values.

11. The blood analysis method according to claim 8, wherein the information regarding a necessity of additional treatment of the blood sample is acquired as the information related to the number of platelets in the blood sample based on the platelets count in the blood sample.

12. The blood analysis method according to claim 3, wherein the coagulation end point is an end point of a time range used for calculating the coagulation time of the blood sample.

13. The blood analysis method according to claim 12, wherein a start point of the predetermined time range is set after the coagulation end point.

14. The blood analysis method according to claim 13, wherein a length of the predetermined time range is 5 seconds or more and 10 seconds or less.

15. The blood analysis method according to claim 1, wherein the information related to the number of platelets in the blood sample includes the number of platelets or information related to necessity of additional treatment on the blood sample.

16. The blood analysis method according to claim 1, wherein the information related to the number of platelets in the blood sample is displayed on a display means.

17. The blood analysis method according to claim 1, wherein the optical information is acquired in a step of measuring the coagulation time of the blood sample.

18. A blood analyzer comprising:
    a measuring unit for irradiating light to a mixed liquid in which a blood sample and a reagent for coagulation time measurement are mixed, and for detecting light generated from the mixed liquid; and
    a processing unit for processing a result detected by the measuring unit;
    wherein the processing unit acquires optical information which changes over time from the mixed liquid after mixing the blood sample and the reagent; and
    acquires information related to a coagulation time and information related to a number of platelets in the blood sample based on the acquired optical information,
    wherein the optical information comprises data indicating an intensity of transmission light, an intensity of scattered light or light absorbance,
    the information related to the coagulation time comprises the coagulation time or a concentration obtained based on the coagulation time, and the information related to the number of platelets comprises a number of platelets, information regarding a necessity of additional treatment on the blood sample, or a level of platelet count, and wherein the information related to the number of platelets in the blood sample is acquired based on the optical information in a predetermined time range including a timing after a coagulation end point.

19. A non-transitory computer readable medium storing programs executable by a processor to:

acquire optical information which changes over time from a mixed liquid of a blood sample and a reagent for coagulation time measurement after mixing the blood sample and the reagent; and acquire information related to a coagulation time and information related to a number of platelets in the blood sample based on the acquired optical information, wherein the optical information comprises data indicating an intensity of transmission light, an intensity of scattered light or light absorbance, the information related to the coagulation time comprises the coagulation time or a concentration obtained based on the coagulation time, and the information related to the number of platelets comprises a number of platelets, information regarding a necessity of additional treatment on the blood sample, or a level of platelet count, and wherein the information related to the number of platelets in the blood sample is acquired based on the optical information in a predetermined time range including a timing after a coagulation end point.

\* \* \* \* \*